US008696708B2

(12) United States Patent
Lechmann et al.

(10) Patent No.: US 8,696,708 B2
(45) Date of Patent: Apr. 15, 2014

(54) FACET INTERFERENCE SCREW

(75) Inventors: Beat Lechmann, Grenchen (CH); Paul W. Pavlov, Nijmegen (NL); Silas Zurschmiede, Grenchen (CH)

(73) Assignee: DePuy Synthes Products, LLC, Raynham, MA (US)

( * ) Notice: Subject to any disclaimer, the term of this patent is extended or adjusted under 35 U.S.C. 154(b) by 100 days.

(21) Appl. No.: 12/920,340

(22) PCT Filed: Mar. 5, 2009

(86) PCT No.: PCT/US2009/036175
§ 371 (c)(1),
(2), (4) Date: Aug. 31, 2010

(87) PCT Pub. No.: WO2009/111632
PCT Pub. Date: Sep. 11, 2009

(65) Prior Publication Data
US 2011/0004247 A1 Jan. 6, 2011

Related U.S. Application Data
(60) Provisional application No. 61/034,295, filed on Mar. 6, 2008.

(51) Int. Cl.
A61B 17/70 (2006.01)

(52) U.S. Cl.
USPC .......................................... 606/247; 606/279

(58) Field of Classification Search
USPC ......... 606/247, 301, 304, 309, 315, 318, 321, 606/328, 279; 411/383, 385; 433/172–175, 433/177, 182, 201.1, 202.1, 215, 220, 221; 623/17.11–17.16
See application file for complete search history.

(56) References Cited

U.S. PATENT DOCUMENTS

| 4,344,190 A | 8/1982 | Lee et al. |
| 4,501,269 A | 2/1985 | Bagby |

(Continued)

FOREIGN PATENT DOCUMENTS

| EP | 0 857 465 | 8/1998 |
| EP | 2249730 | 11/2010 |

(Continued)

OTHER PUBLICATIONS

U.S. Appl. No. 13/180,422, filed Jul. 11, 2011, Angert.
International Patent Application No. PCT/US2009/036175: International Search Report dated Jul. 27, 2009, 18 pages.

Primary Examiner — Eduardo C Robert
Assistant Examiner — Atiya Mahmud
(74) Attorney, Agent, or Firm — Baker & Hostetler LLP

(57) ABSTRACT

A facet interference screw (10) for insertion between the facet joints of adjacent superior and inferior vertebrae includes an externally threaded shaft portion and a head. The facet interference screw is preferably split into first (20) and second (30) components, each including an outer, semicircular externally threaded surface (22, 32) so that when coupled together the semicircular externally threaded surfaces form the externally threaded shaft portion. The inner surfaces (24, 34) of the first and second components may include curved contacting surfaces so that when inserted, the first component is movable with respect to the second component. Alternatively, the screw may include a damping component (60a') between the inner surfaces of the first and second components to facilitate damping of the first and second components with respect to one another. The damping component preferably also facilitates articulated motion of the first and second components.

23 Claims, 13 Drawing Sheets

(56) References Cited

U.S. PATENT DOCUMENTS

| | | |
|---|---|---|
| 4,754,749 A | 7/1988 | Tsou |
| 4,878,915 A | 11/1989 | Brantigan |
| 4,898,186 A | 2/1990 | Ikada et al. |
| 4,940,467 A | 7/1990 | Tronzo |
| 5,015,247 A | 5/1991 | Michelson |
| 5,122,132 A | 6/1992 | Bremer |
| 5,334,204 A | 8/1994 | Clewett et al. |
| 5,527,312 A | 6/1996 | Ray |
| 5,571,191 A | 11/1996 | Fitz |
| 5,593,409 A | 1/1997 | Michelson |
| 5,669,909 A * | 9/1997 | Zdeblick et al. ............... 606/247 |
| 5,709,687 A | 1/1998 | Pennig |
| 5,772,661 A | 6/1998 | Michelson |
| 5,928,284 A | 7/1999 | Mehdizadeh |
| 6,014,588 A | 1/2000 | Fitz |
| 6,039,762 A | 3/2000 | McKay |
| 6,045,580 A | 4/2000 | Scarborough et al. |
| 6,056,192 A | 5/2000 | Cameron |
| RE36,758 E | 6/2000 | Fitz |
| 6,077,267 A | 6/2000 | Huene |
| 6,099,529 A | 8/2000 | Gertzman et al. |
| 6,117,162 A | 9/2000 | Schmieding et al. |
| 6,132,464 A | 10/2000 | Martin |
| 6,162,225 A | 12/2000 | Gertzman et al. |
| 6,200,347 B1 | 3/2001 | Anderson et al. |
| 6,210,412 B1 | 4/2001 | Michelson |
| 6,280,447 B1 | 8/2001 | Marino et al. |
| 6,371,986 B1 | 4/2002 | Bagby |
| 6,419,703 B1 | 7/2002 | Fallin et al. |
| 6,419,706 B1 | 7/2002 | Graf |
| 6,485,518 B1 | 11/2002 | Cornwall et al. |
| 6,494,883 B1 | 12/2002 | Ferree |
| 6,506,192 B1 | 1/2003 | Gertzman et al. |
| 6,540,747 B1 | 4/2003 | Marino |
| 6,547,795 B2 | 4/2003 | Schneiderman |
| 6,565,605 B2 | 5/2003 | Goble et al. |
| 6,579,319 B2 | 6/2003 | Goble et al. |
| 6,610,091 B1 | 8/2003 | Reiley |
| 6,648,893 B2 | 11/2003 | Dudasik |
| 6,669,729 B2 | 12/2003 | Chin |
| 6,685,706 B2 | 2/2004 | Padget et al. |
| 6,740,093 B2 | 5/2004 | Hochschuler et al. |
| 6,811,567 B2 | 11/2004 | Reiley |
| 6,902,578 B1 | 6/2005 | Anderson et al. |
| 6,902,580 B2 | 6/2005 | Fallin et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,041,136 B2 | 5/2006 | Goble et al. |
| 7,051,451 B2 | 5/2006 | Augostino et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,074,237 B2 | 7/2006 | Goble et al. |
| 7,074,238 B2 | 7/2006 | Stinson et al. |
| 7,083,622 B2 | 8/2006 | Simonson |
| 7,087,084 B2 | 8/2006 | Reiley |
| 7,090,698 B2 | 8/2006 | Goble et al. |
| 7,094,239 B1 | 8/2006 | Michelson |
| 7,101,398 B2 | 9/2006 | Dooris et al. |
| 7,147,664 B2 | 12/2006 | Louis et al. |
| 7,220,262 B1 | 5/2007 | Hynes |
| 7,223,269 B2 | 5/2007 | Chappuis |
| 7,261,716 B2 | 8/2007 | Strobel et al. |
| 7,282,064 B2 | 10/2007 | Chin |
| 7,371,238 B2 | 5/2008 | Soboleski et al. |
| D574,495 S | 8/2008 | Petersen |
| 7,406,775 B2 | 8/2008 | Funk et al. |
| D581,538 S | 11/2008 | Horton |
| 7,445,635 B2 | 11/2008 | Fallin et al. |
| 7,452,369 B2 | 11/2008 | Barry |
| 7,491,236 B2 | 2/2009 | Cragg et al. |
| D589,626 S | 3/2009 | Petersen |
| D603,502 S | 11/2009 | Petersen |
| 7,699,878 B2 | 4/2010 | Pavlov et al. |
| 7,708,761 B2 | 5/2010 | Petersen |
| 7,708,766 B2 | 5/2010 | Anderson et al. |
| 7,837,713 B2 | 11/2010 | Petersen |
| 2003/0208202 A1 | 11/2003 | Falahee |
| 2004/0006391 A1 | 1/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0087948 A1 | 5/2004 | Suddaby |
| 2004/0127906 A1 * | 7/2004 | Culbert et al. ................. 606/72 |
| 2004/0143268 A1 | 7/2004 | Falahee |
| 2004/0186475 A1 | 9/2004 | Falahee |
| 2004/0215344 A1 | 10/2004 | Hochschuler et al. |
| 2004/0230201 A1 | 11/2004 | Yuan et al. |
| 2004/0230304 A1 | 11/2004 | Yuan et al. |
| 2004/0254575 A1 | 12/2004 | Obenchain et al. |
| 2005/0015150 A1 | 1/2005 | Lee |
| 2005/0027361 A1 | 2/2005 | Reiley |
| 2005/0038438 A1 | 2/2005 | Anderson et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080486 A1 | 4/2005 | Fallin et al. |
| 2005/0085912 A1 | 4/2005 | Arnin et al. |
| 2005/0101953 A1 | 5/2005 | Simonson |
| 2005/0101954 A1 | 5/2005 | Simonson |
| 2005/0101956 A1 | 5/2005 | Simonson |
| 2005/0119748 A1 | 6/2005 | Reiley et al. |
| 2005/0124993 A1 | 6/2005 | Chappuis |
| 2005/0131405 A1 | 6/2005 | Molz, IV et al. |
| 2005/0131406 A1 | 6/2005 | Reiley et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149030 A1 | 7/2005 | Serhan et al. |
| 2005/0149190 A1 | 7/2005 | Reiley |
| 2005/0159746 A1 | 7/2005 | Grob et al. |
| 2005/0177240 A1 | 8/2005 | Blain |
| 2005/0197700 A1 | 9/2005 | Boehm, Jr. et al. |
| 2005/0203625 A1 * | 9/2005 | Boehm et al. ............. 623/17.11 |
| 2005/0209694 A1 | 9/2005 | Loeb |
| 2005/0234552 A1 | 10/2005 | Reiley |
| 2005/0240188 A1 | 10/2005 | Chow et al. |
| 2005/0240264 A1 | 10/2005 | Tokish, Jr. et al. |
| 2005/0240265 A1 | 10/2005 | Kuiper et al. |
| 2005/0240266 A1 | 10/2005 | Kuiper et al. |
| 2005/0251256 A1 | 11/2005 | Reiley |
| 2005/0261770 A1 | 11/2005 | Kuiper et al. |
| 2005/0267480 A1 | 12/2005 | Suddaby |
| 2005/0267579 A1 | 12/2005 | Reiley et al. |
| 2005/0273167 A1 | 12/2005 | Triplett et al. |
| 2005/0277921 A1 | 12/2005 | Eisermann et al. |
| 2005/0277930 A1 | 12/2005 | Parsons |
| 2005/0277938 A1 | 12/2005 | Parsons |
| 2005/0283238 A1 | 12/2005 | Reiley |
| 2006/0004367 A1 | 1/2006 | Alamin et al. |
| 2006/0004449 A1 | 1/2006 | Goble et al. |
| 2006/0004451 A1 | 1/2006 | Goble et al. |
| 2006/0009847 A1 | 1/2006 | Reiley |
| 2006/0009848 A1 | 1/2006 | Reiley |
| 2006/0009849 A1 | 1/2006 | Reiley |
| 2006/0036243 A1 | 2/2006 | Sasso et al. |
| 2006/0036323 A1 | 2/2006 | Carl et al. |
| 2006/0041311 A1 | 2/2006 | McLeer |
| 2006/0052785 A1 | 3/2006 | Augostino et al. |
| 2006/0064099 A1 | 3/2006 | Pavlov et al. |
| 2006/0079896 A1 | 4/2006 | Kwak et al. |
| 2006/0084976 A1 | 4/2006 | Borgstrom et al. |
| 2006/0085075 A1 | 4/2006 | McLeer |

(56) References Cited

U.S. PATENT DOCUMENTS

| | | |
|---|---|---|
| 2006/0100707 A1 | 5/2006 | Stinson et al. |
| 2006/0100709 A1 | 5/2006 | Reiley |
| 2006/0111779 A1 | 5/2006 | Petersen |
| 2006/0111780 A1 | 5/2006 | Petersen |
| 2006/0111781 A1 | 5/2006 | Petersen |
| 2006/0111782 A1 | 5/2006 | Petersen |
| 2006/0129239 A1 | 6/2006 | Kwak |
| 2006/0149229 A1 | 7/2006 | Kwak et al. |
| 2006/0149230 A1 | 7/2006 | Kwak et al. |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0149375 A1 | 7/2006 | Yuan et al. |
| 2006/0184180 A1 | 8/2006 | Augostino et al. |
| 2006/0190081 A1 | 8/2006 | Kraus et al. |
| 2006/0200137 A1 | 9/2006 | Soboleski et al. |
| 2006/0200149 A1 | 9/2006 | Hoy et al. |
| 2006/0212034 A1 | 9/2006 | Triplett et al. |
| 2006/0217718 A1 | 9/2006 | Chervitz et al. |
| 2006/0235391 A1 | 10/2006 | Sutterlin, III |
| 2006/0235414 A1* | 10/2006 | Lim et al. ................ 606/73 |
| 2006/0241597 A1 | 10/2006 | Mitchell et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247769 A1 | 11/2006 | Molz et al. |
| 2006/0259142 A1 | 11/2006 | Dooris et al. |
| 2006/0264954 A1 | 11/2006 | Sweeney, II et al. |
| 2006/0265069 A1 | 11/2006 | Goble et al. |
| 2006/0265070 A1 | 11/2006 | Stinson et al. |
| 2006/0271046 A1 | 11/2006 | Kwak et al. |
| 2006/0271195 A1 | 11/2006 | Thramann |
| 2006/0276790 A1 | 12/2006 | Dawson et al. |
| 2006/0282080 A1 | 12/2006 | Albert et al. |
| 2007/0005137 A1 | 1/2007 | Kwak |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0016296 A1 | 1/2007 | Triplett et al. |
| 2007/0016297 A1 | 1/2007 | Johnson |
| 2007/0030221 A1* | 2/2007 | Pak et al. ................ 345/87 |
| 2007/0035795 A1 | 2/2007 | Hubbard |
| 2007/0055236 A1 | 3/2007 | Hudgins et al. |
| 2007/0055245 A1 | 3/2007 | Sasso et al. |
| 2007/0055257 A1* | 3/2007 | Vaccaro et al. ................ 606/73 |
| 2007/0055373 A1 | 3/2007 | Hudgins et al. |
| 2007/0073290 A1 | 3/2007 | Boehm, Jr. |
| 2007/0073396 A1 | 3/2007 | Arnin |
| 2007/0079517 A1 | 4/2007 | Augostino et al. |
| 2007/0083266 A1 | 4/2007 | Lang |
| 2007/0088358 A1 | 4/2007 | Yuan et al. |
| 2007/0088440 A1* | 4/2007 | Eisermann et al. ........ 623/17.14 |
| 2007/0093833 A1 | 4/2007 | Kuiper et al. |
| 2007/0112428 A1 | 5/2007 | Lancial |
| 2007/0118218 A1 | 5/2007 | Hooper |
| 2007/0118224 A1* | 5/2007 | Shah et al. ................ 623/17.15 |
| 2007/0123863 A1 | 5/2007 | Winslow et al. |
| 2007/0123891 A1 | 5/2007 | Ries et al. |
| 2007/0123892 A1 | 5/2007 | Ries et al. |
| 2007/0135814 A1 | 6/2007 | Farris |
| 2007/0149976 A1 | 6/2007 | Hale et al. |
| 2007/0149983 A1 | 6/2007 | Link |
| 2007/0156237 A1 | 7/2007 | Kwak |
| 2007/0167946 A1 | 7/2007 | Triplett et al. |
| 2007/0168029 A1 | 7/2007 | Yuan et al. |
| 2007/0168035 A1 | 7/2007 | Koske |
| 2007/0179617 A1 | 8/2007 | Brown et al. |
| 2007/0179619 A1 | 8/2007 | Grob et al. |
| 2007/0185492 A1 | 8/2007 | Chervitz et al. |
| 2007/0185576 A1 | 8/2007 | Goble et al. |
| 2007/0198091 A1 | 8/2007 | Boyer et al. |
| 2007/0227547 A1 | 10/2007 | Trieu |
| 2007/0233092 A1 | 10/2007 | Falahee |
| 2007/0233093 A1 | 10/2007 | Falahee |
| 2007/0233256 A1 | 10/2007 | Ohrt et al. |
| 2007/0244483 A9 | 10/2007 | Winslow et al. |
| 2007/0250166 A1 | 10/2007 | McKay |
| 2007/0255224 A1 | 11/2007 | Ahern et al. |
| 2007/0255411 A1 | 11/2007 | Reiley |
| 2007/0265706 A1 | 11/2007 | Reiley |
| 2007/0270967 A1 | 11/2007 | Fallin et al. |
| 2007/0276374 A1 | 11/2007 | Broman et al. |
| 2007/0282445 A1 | 12/2007 | Reiley |
| 2008/0015583 A1 | 1/2008 | Reiley |
| 2008/0015585 A1 | 1/2008 | Berg et al. |
| 2008/0015696 A1 | 1/2008 | Reiley |
| 2008/0021457 A1 | 1/2008 | Anderson et al. |
| 2008/0027543 A1 | 1/2008 | Eisermann et al. |
| 2008/0045954 A1 | 2/2008 | Reiley et al. |
| 2008/0065076 A1 | 3/2008 | Cragg et al. |
| 2008/0125855 A1* | 5/2008 | Henkes et al. ................ 623/1.18 |
| 2008/0200953 A1 | 8/2008 | Reiley et al. |
| 2008/0208249 A1 | 8/2008 | Blain et al. |
| 2008/0208341 A1 | 8/2008 | McCormack et al. |
| 2008/0221622 A1 | 9/2008 | Triplett et al. |
| 2008/0221692 A1* | 9/2008 | Zucherman et al. ........ 623/17.16 |
| 2008/0234735 A1 | 9/2008 | Joshi |
| 2008/0234758 A1* | 9/2008 | Fisher et al. ................ 606/309 |
| 2008/0249568 A1 | 10/2008 | Kuiper et al. |
| 2008/0249571 A1 | 10/2008 | Sasso et al. |
| 2008/0255618 A1 | 10/2008 | Fisher et al. |
| 2008/0255619 A1 | 10/2008 | Schneiderman et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0262545 A1 | 10/2008 | Simonson |
| 2008/0262555 A1 | 10/2008 | Assell et al. |
| 2008/0269897 A1 | 10/2008 | Joshi |
| 2008/0275505 A1 | 11/2008 | Yuan et al. |
| 2008/0275507 A1 | 11/2008 | Triplett et al. |
| 2008/0287959 A1 | 11/2008 | Quest et al. |
| 2008/0287996 A1 | 11/2008 | Soboleski et al. |
| 2008/0292161 A1 | 11/2008 | Funk et al. |
| 2008/0306537 A1 | 12/2008 | Culbert |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0005818 A1 | 1/2009 | Chin et al. |
| 2009/0012566 A1 | 1/2009 | Fauth |
| 2009/0018585 A1 | 1/2009 | Reiley |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0024219 A1 | 1/2009 | McLeer |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036927 A1 | 2/2009 | Vestgaarden |
| 2009/0076551 A1 | 3/2009 | Petersen |
| 2009/0082868 A1* | 3/2009 | Cordaro et al. ............ 623/17.16 |
| 2009/0105819 A1 | 4/2009 | Barry |
| 2009/0234397 A1 | 9/2009 | Petersen |

FOREIGN PATENT DOCUMENTS

| | | |
|---|---|---|
| JP | 2003/512090 A | 4/2003 |
| WO | WO 00/04851 | 2/2000 |
| WO | WO 01/15638 A1 | 3/2001 |
| WO | WO 2004/043278 | 5/2004 |
| WO | WO 2006/119088 A2 | 11/2006 |
| WO | WO 2007/120903 | 10/2007 |
| WO | WO 2009/111632 | 9/2009 |

* cited by examiner

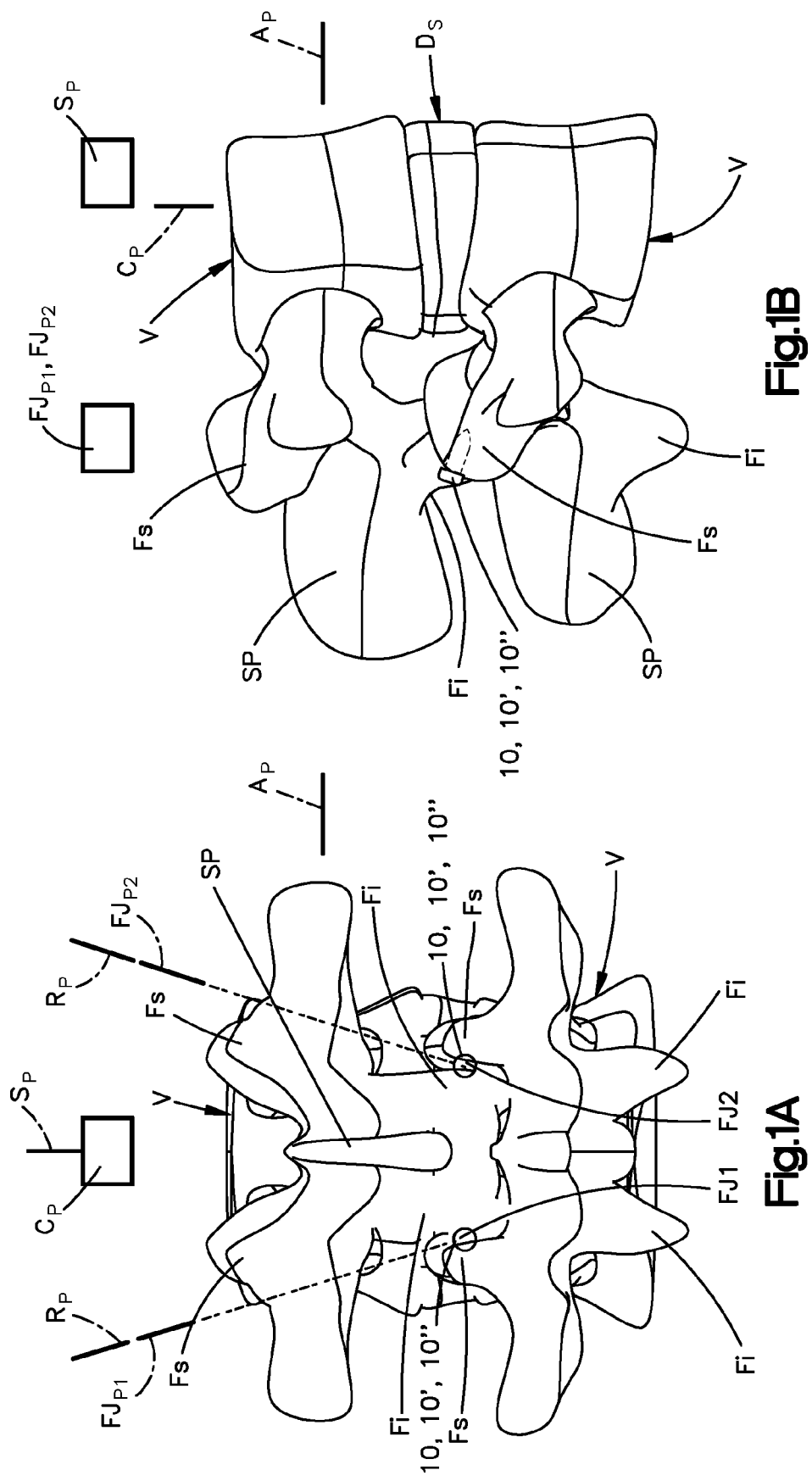

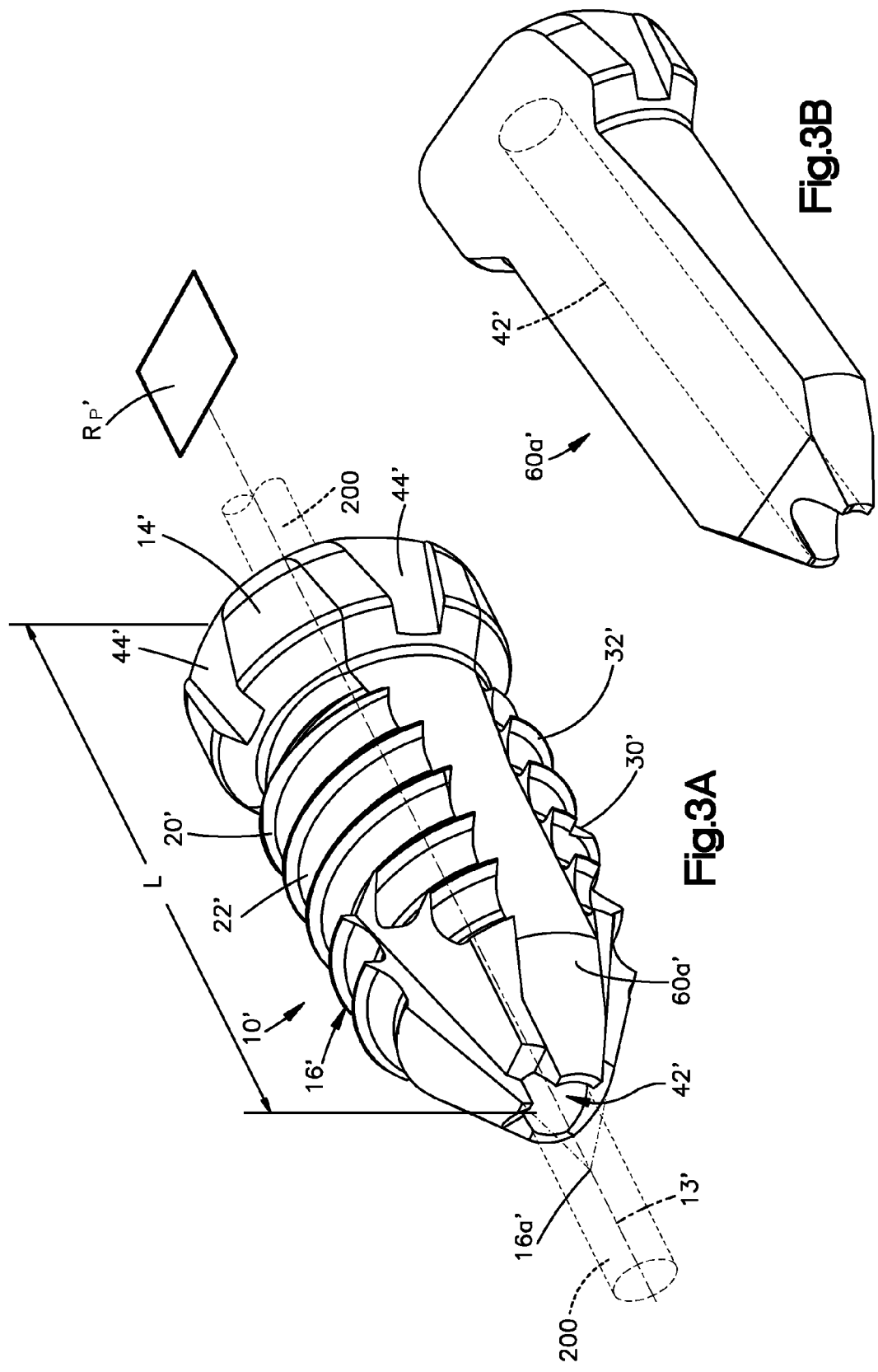

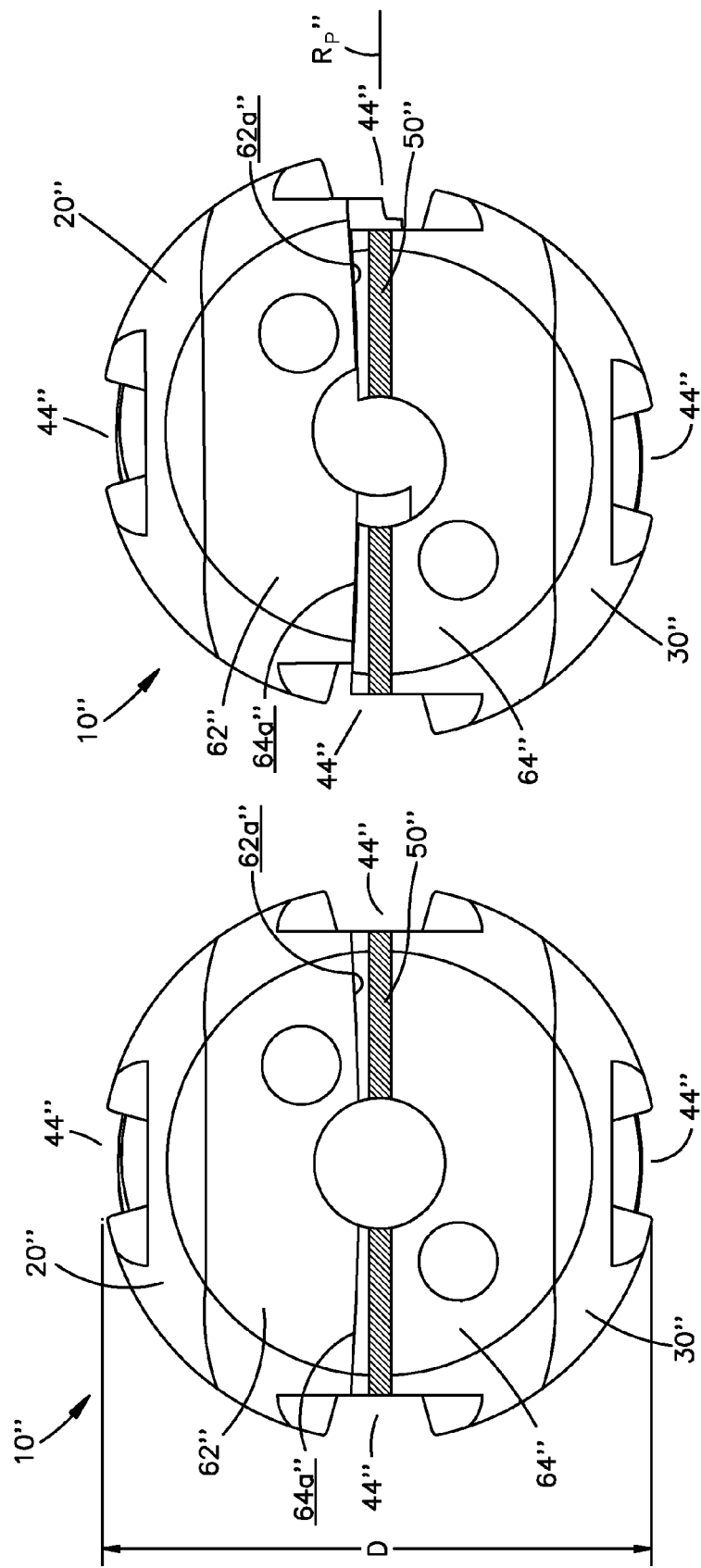

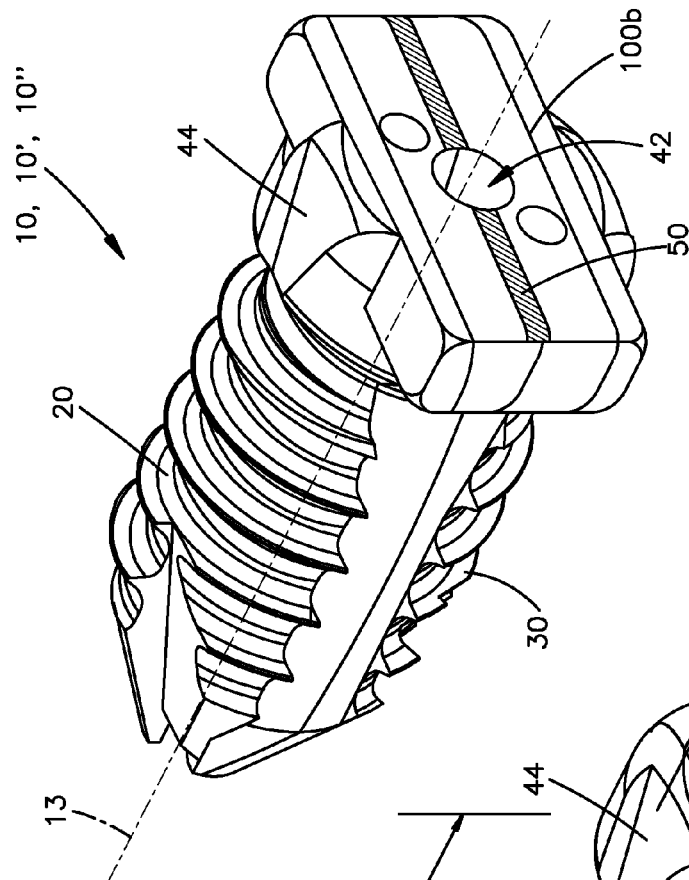
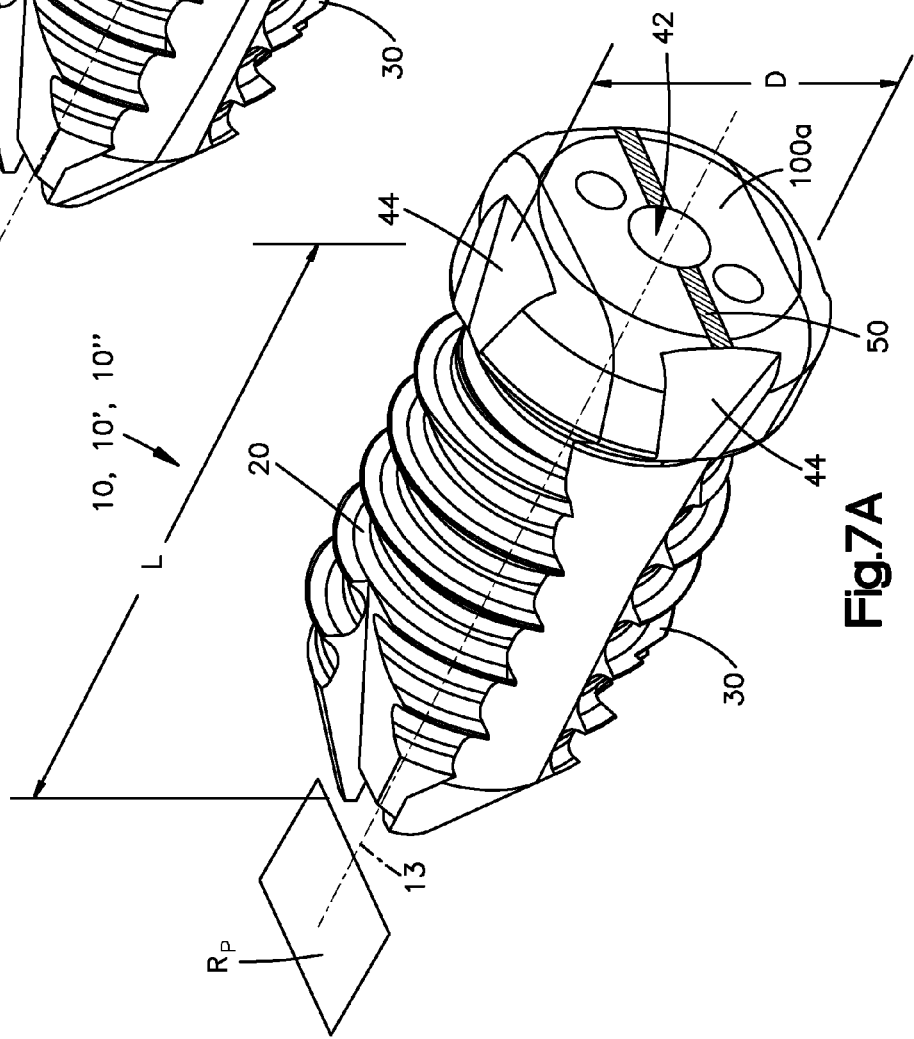
Fig.7A
Fig.7B

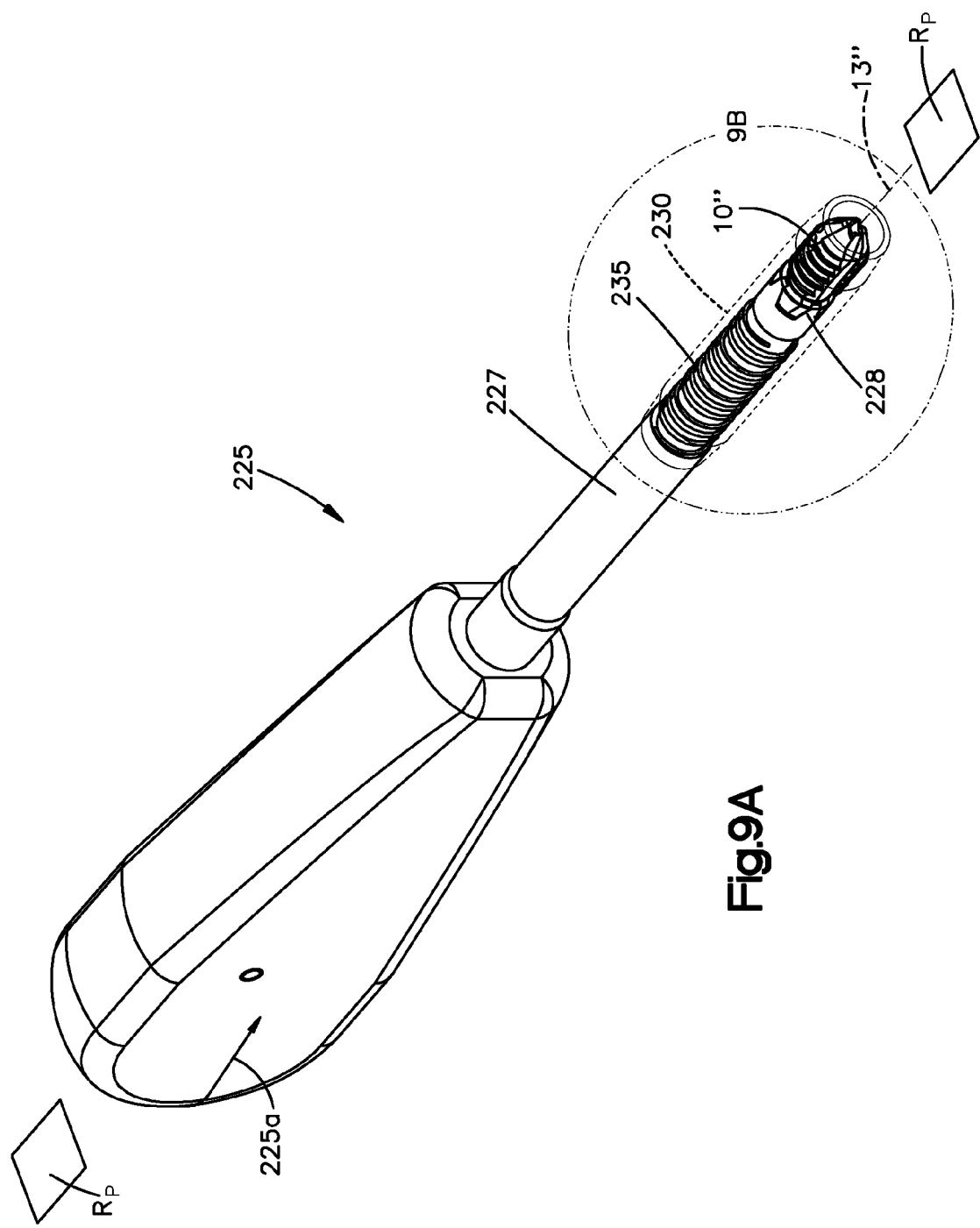

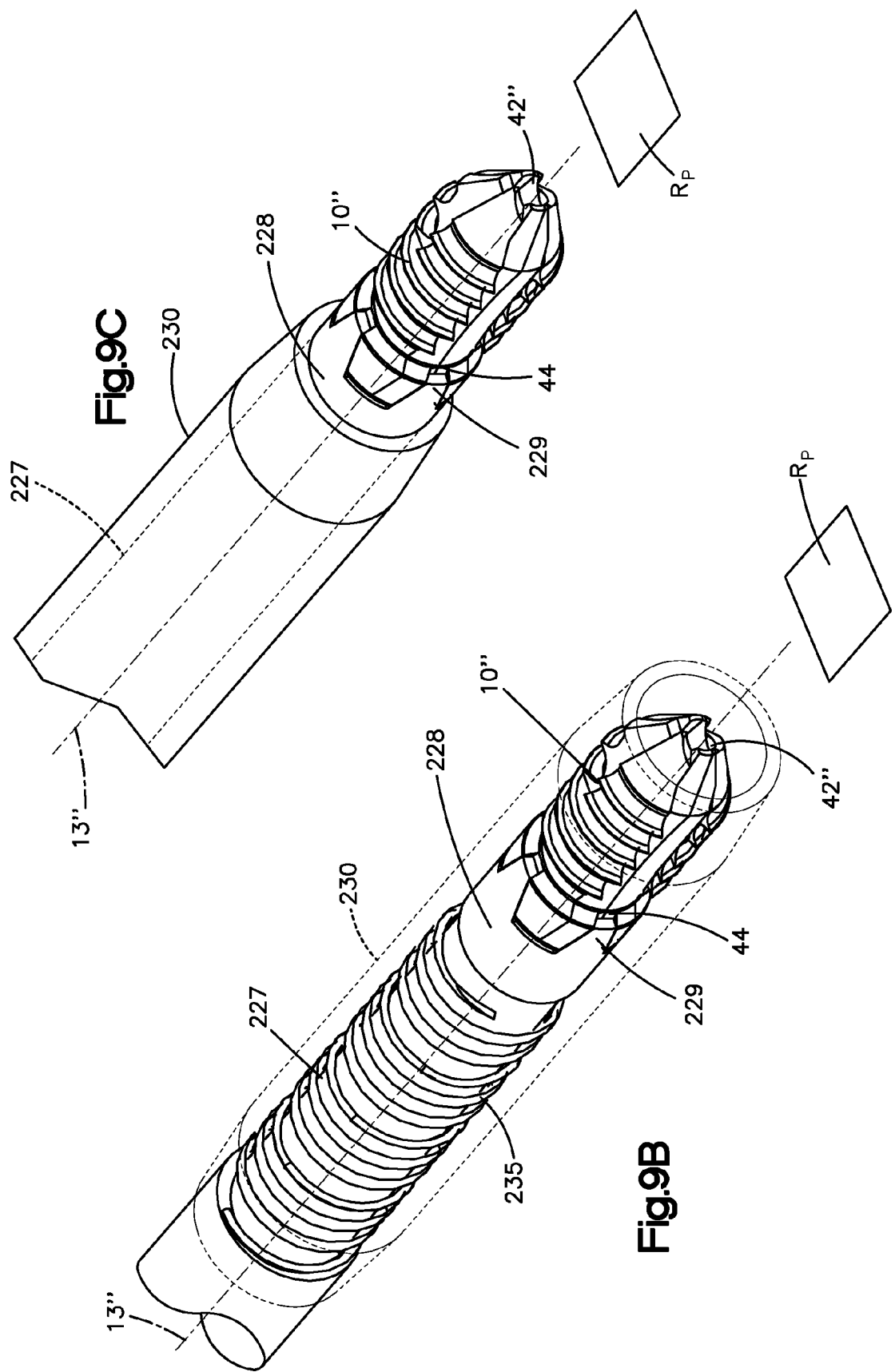

FACET INTERFERENCE SCREW

CROSS-REFERENCE TO RELATED APPLICATIONS

This application is the National Stage of International Application No. PCT/US2009/036175, filed Mar. 5, 2009, which claims the benefit of U.S. Provisional Application No. 61/034,295, filed Mar. 6, 2008, the disclosures of which are incorporated herein by reference in their entireties for all purposes.

BACKGROUND OF THE INVENTION

The facet joint is an articulating joint of a spinal motion segment that can degenerate during aging, trauma, typical use and other factors. The facet joints in various regions of the spine are oriented in different planes, for example, the lumbar facet joints are generally located in the sagittal plane $S_P$, the thoracic facet joints are generally oriented in the coronal plane $C_P$ and the cervical facet joints are generally oriented in the axial or transverse plane $A_P$ (FIGS. 1 and 2). These orientations facilitate different types of motion in the respective regions of the spine.

Degenerated facet joints are often painful as a result of, for example, wear between two arthritic articulating surfaces that surround the synovial joint capsule. The surfaces of the facet joints are covered by articular cartilage. Inflammatory reactions may occur when the cartilaginous surfaces of the facets become degraded or fissured, thereby leading to direct bone-on-bone contact and resulting in pain. Over distraction of the surrounding joint capsules may also cause pain to the patient. Patients typically undergo a fusion surgery to alleviate this pain.

It is desirable to develop an implant for insertion into the facet joints between adjacent superior and inferior vertebrae to alleviate pain resulting from degenerating facet joints that may not result in immediate fusion of the facet joint.

BRIEF SUMMARY OF THE INVENTION

The present invention relates to a spinal implant. More specifically, a preferred embodiment of the present invention relates to a facet interference screw for insertion between the facet joints of adjacent superior and inferior vertebrae. The facet interference screw preferably includes a head portion and an externally threaded shaft portion so that the facet interference screw can be rotatively inserted or screwed into the facet joint via an insertion instrument such as, for example, a screw driver or screw driver-like instrument. The facet interference screw preferably includes first and second components such that each of the first and second components includes an outer, semicircular externally threaded surface and an inner surface so that when coupled together the semicircular externally threaded surfaces form an externally threaded shaft portion.

In a preferred embodiment, the inner surfaces of the first and second components may include curved contacting surfaces. The curved contacting surfaces preferably permit an arcuate movement between the first and second components along a longitudinal axis and limited movement lateral to the longitudinal axis.

In another preferred embodiment of the facet interference screw, a damping component may be inserted between the inner surfaces of the first and second components to facilitate damping of the first and second components with respect to one another. The damping component may be in the form of a two-piece damping component including an upper damping component having an outer surface for contacting the inner surface of the first component and an inner surface. The damping component may also include a lower damping component having an outer surface for contacting the inner surface of the second component and an inner surface. The inner surfaces of the upper and lower damping components each include a curved contacting surface so that the upper damping component is articulatable with respect to the lower damping component. The upper damping component is preferably fixed to the first component and the lower damping component is preferably fixed to the second component such that a majority of the articulation of the facet interference screw is between the upper and lower damping components at the curved contacting surfaces of the upper and lower damping components.

The present invention is also related a method for inserting the preferred facet interference screw between the facet joints of adjacent superior and inferior vertebrae.

BRIEF DESCRIPTION OF THE DRAWINGS

The foregoing summary, as well as the following detailed description of preferred embodiments of the application, will be better understood when read in conjunction with the appended drawings. For the purposes of illustrating the preferred facet interference screw and surgical method for inserting the facet interference screw of the present application, there are shown in the drawings preferred embodiments. It should be understood, however, that the application is not limited to the precise arrangements and instrumentalities shown. In the drawings:

FIG. 1A illustrates a rear perspective view of two facet interference screws mounted in facet joints in a mounted position in a lumbar portion of a patient's spine in accordance with one of the below-described preferred embodiments of the present invention;

FIG. 1B illustrates a side perspective view of the facet interference screws in the mounted position shown in FIG. 1A;

FIG. 3A illustrates a top perspective view of a facet interference screw according to a second preferred embodiment of the present invention;

FIG. 3B illustrates a top perspective view of a damping component that may be used in connection with the facet interference screw shown in FIG. 3A, the damping component including a cannulated opening therethrough;

FIG. 6A illustrates a rear elevational view of the facet interference screw shown in FIG. 4A, the facet interference screw shown in a neutral position;

FIG. 6B illustrates a rear elevational view of the facet interference screw shown in FIG. 4A, the facet interference screw shown undergoing lateral bending;

FIG. 7A illustrates a rear perspective view of one of the above-described facet interference screws of the first, second and third preferred embodiments including a preferred anti-rotational mechanism;

FIG. 7B illustrates a rear perspective view of one of the above-described facet interference screws of the first, second and third preferred embodiments including an alternative preferred anti-rotational mechanism;

FIG. 9A illustrates a top perspective view of the facet interference screw of FIG. 4A mounted to a preferred screw driver, wherein a preferred sleeve, shown in phantom, of the screw driver is in an extended position;

FIG. 9B illustrates a top perspective view of the facet interference screw of FIG. 4A, taken from within circle 9B of FIG. 9A;

FIG. 9C illustrates a side perspective view of the facet interference screw of FIG. 4A mounted to the screw driver with the sleeve in a retracted position.

DETAILED DESCRIPTION OF THE INVENTION

Figure 2A:
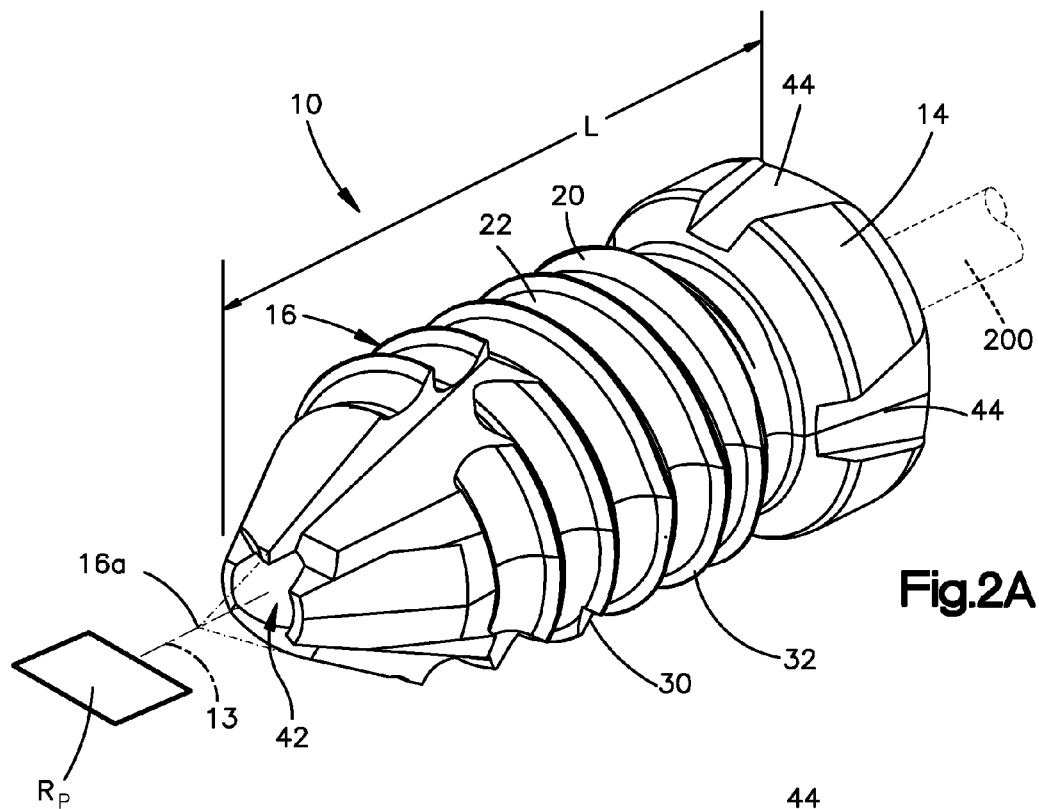
FIG. 2A illustrates a side perspective view of a facet interference screw according to a first preferred embodiment of the present invention.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the facet interference screw and designated parts thereof. The words, "anterior", "posterior", "superior", "inferior", "lateral", "sagittal", "axial", "coronal" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. Preferred embodiments of the present invention are directed to (i) first, second and third preferred embodiments of a facet interference screw 10, 10', 10" for insertion between facet joints FJ of adjacent superior and inferior vertebrae V and (ii) an exemplary surgical method for inserting the preferred facet interference screws 10, 10', 10" between the facet joints FJ of adjacent superior and inferior vertebrae V in a patient's spine. It should be appreciated that while the preferred facet interference screws 10, 10', 10" of the present application will be described as and may generally be used in the spine (for example, in the lumbar, thoracic or cervical regions), one of ordinary skill in the art will understand that the preferred facet interference screws 10, 10', 10", as well as the components thereof, may be used in other parts of the body including, for example, the knee, hip, shoulder, finger, joints, long bones or bones in the hand, face, feet, including, for example, metacarpal, trapecoidal, and scaphoidal joints of the hand and metatarsal-phalanges joints in the feet, etc.

Referring to FIGS. 1A and 1B, two exemplary vertebrae V in the lumbar region of a patient's spine are shown. The vertebrae V each include a pair of superior articular facets $F_S$ and a pair of inferior articular facets $F_i$ on either side of the spinous process SP. The inferior facet $F_i$ on the superior vertebra V and the superior facet $F_S$ on the inferior vertebra V are movably interconnected via a joint capsule or facet joint space $FJ_1$, $FJ_2$ that guide and limit motion of the motion segment. The vertebrae V shown in FIGS. 1A and 1B include a first facet joint $FJ_1$ positioned to a left-side of the spinous process SP and a second facet joint $FJ_2$ positioned to a right-side of the spinous process $S_P$. The first and second facet joints $FJ_1$, $FJ_2$ include first and second facet joint planes $FJ_{P1}$, $FJ_{P2}$, respectively, that are generally oriented in the sagittal plane $S_P$ in a majority of the lumbar spine.

The facet joints $FJ_1$, $FJ_2$ guide and facilitate movement between the superior and inferior vertebrae V. As a result of natural or traumatic degeneration of the spine S, the facet joints $FJ_1$, $FJ_2$ may be affected. For example, an inflammatory reaction may occur when the cartilaginous surfaces of the facet joints $FJ_1$, $FJ_2$ are degraded, which may lead to direct contact between the inferior facet $F_i$ formed on the superior vertebra V and the superior facet $F_S$ formed on the inferior vertebra V, resulting in pain in the facet joints $FJ_1$, $FJ_2$.

Augmentation of the facet joints $FJ_1$, $FJ_2$ to alleviate pressure on the painful area may be achieved via the insertion of an implant, preferably a preferred facet interference screw 10, 10', 10", between the inferior facet $F_i$ formed on the superior vertebra V and the superior facet $F_S$ formed on the inferior vertebra V. The preferred facet interference screw 10, 10', 10" allows for the treatment of the facet joints $FJ_1$, $FJ_2$, permitting preservation of mobility and/or stabilization while enabling the pedicles to remain intact if additional internal fixation is required at any time. Augmentation of the facet joints $FJ_1$, $FJ_2$ may be achieved via the insertion of two preferred facet interference screws 10, 10', 10", one for each of the facet joints $FJ_1$, $FJ_2$. In addition, the preferred facet interference screw 10, 10', 10" may be inserted with or without insertion of a spacer within the intervertebral disk space $D_S$ between the adjacent vertebrae V.

Figure 2B:
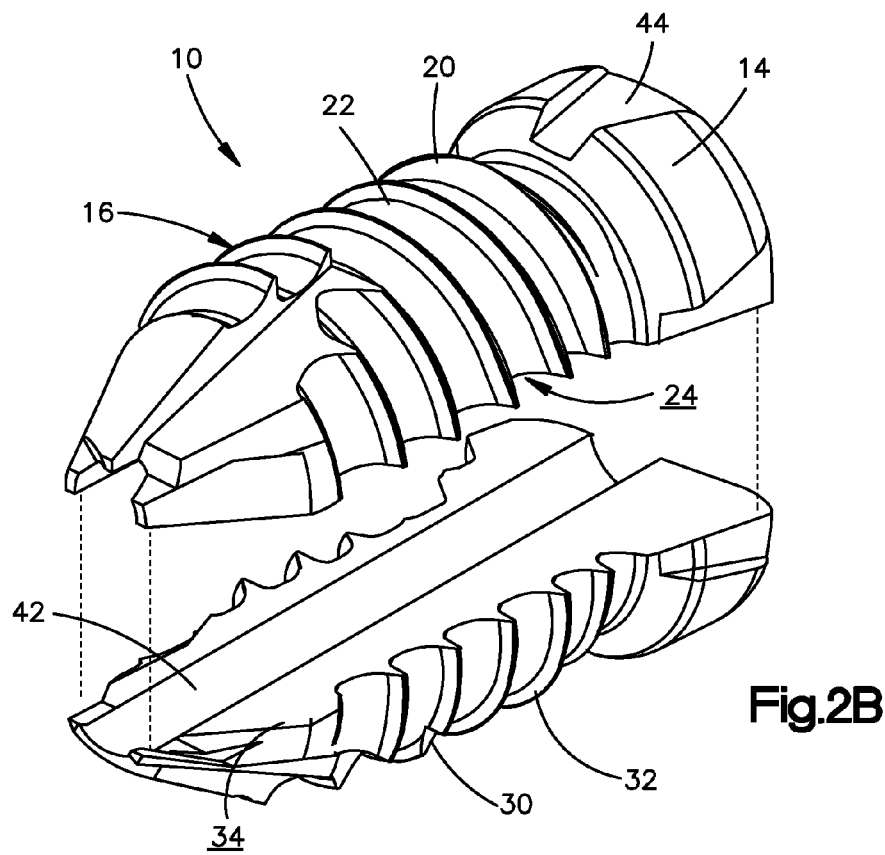
FIG. 2B illustrates an exploded, side perspective view of the facet interference screw shown in FIG. 2A.

Referring to FIGS. 2A and 2B, a first preferred embodiment of the facet interference screw 10 is generally in the form of a bone screw 10. The facet interference screw 10 of the first preferred embodiment includes a head portion 14 and an externally threaded shaft portion 16. The head portion 14 preferably includes a mechanism for engaging a screwdriver 225. For example, the head portion 14 preferably includes a plurality of recesses 44 for engaging a plurality of projections 229 formed on a tip 228 of the screwdriver 225 (as will be described in greater detail below), although other configurations are envisioned, including but not limited to, an internal recess, an external hexagon, a star drive pattern, a Phillips head pattern, a slot for a screw driver, a threading for a correspondingly threaded post, etc. The specific features of the shaft 16 including, for example, thread pitch, self drilling configurations, self tapping configurations, shaft diameter, shaft shape, etc. are interchangeable, and it would be apparent to one having ordinary skill in the art that the facet interference screw 10 is not limited to any particular type of shaft 16 or thread configuration.

The facet interference screw or bone screw 10 of the first preferred embodiment is split longitudinally along a longitudinal axis 13 of the facet interference screw 10, such that the facet interference screw 10 includes a first component 20 and a second component 30. Each of the first and second components 20, 30 includes an outer, preferably semicircular externally threaded surface 22, 32 and an inner surface 24, 34, so that when coupled together the semicircular externally threaded surfaces 22, 32 form the externally threaded shaft portion 16. Thus, in use, the facet interference screw 10 is preferably inserted between the inferior facet $F_i$ formed on the superior vertebra V and the superior facet $F_S$ formed on the inferior vertebra V via rotation by, for example, a screw driver 225, as will be described in greater detail below. The inner surfaces 24, 34 of the first preferred embodiment preferably extend, generally continuously, from the head portion 14 to a tip 16a of the shaft portion 16 and define an articulation plane RP generally along which the first and second components 20, 30 may move relative to each other in a mounted position, as will be described in greater detail below. The inner surfaces 24, 34 are preferably in contact along a substantial portion thereof in an assembled configuration and in the mounted configuration to guide and movement of the first component 20 relative to the second component 30.

The inner surfaces 24, 34 of the first and second components 20, 30 of the facet interference screw 10 of the first preferred embodiment may include curved contacting surfaces having, for example, a convex and/or concave surface for interacting with the curved contacting surface of the other component 20, 30, respectively, so that when inserted, the first component 20 is movable along a curved or arcuate path with respect to the second component 30. That is, for example, the inner surface 24 of the first component 20 may include a convex surface for contacting a concave surface formed on the inner surface 34 of the second component 30. Although as will be appreciated by one of ordinary skill in the art, the inner surface 34 of the second component 30 may have a convex surface while the inner surface 24 of the first component 20 may have a concave surface. Alternatively, both inner surfaces 24, 34 may have a concave surface or a convex surface. The convex or concave shape of the inner surfaces 24, 34 resulting in the arcuate path of movement between the first and second components are preferably mounted in one of the facet joints $FJ_1$, $FJ_2$ in a mounted position to generally mimic the natural arcuate shape of the mating surfaces of the facet joint $FJ_1$, $FJ_2$, as would be apparent to one having ordinary skill in the art.

The inner surfaces 24, 34 of the first and second component 20, 30 may also include a cannulated opening 42 for receipt of a guide wire 200 (FIG. 8), as will be described in greater detail below.

Figure 2C:
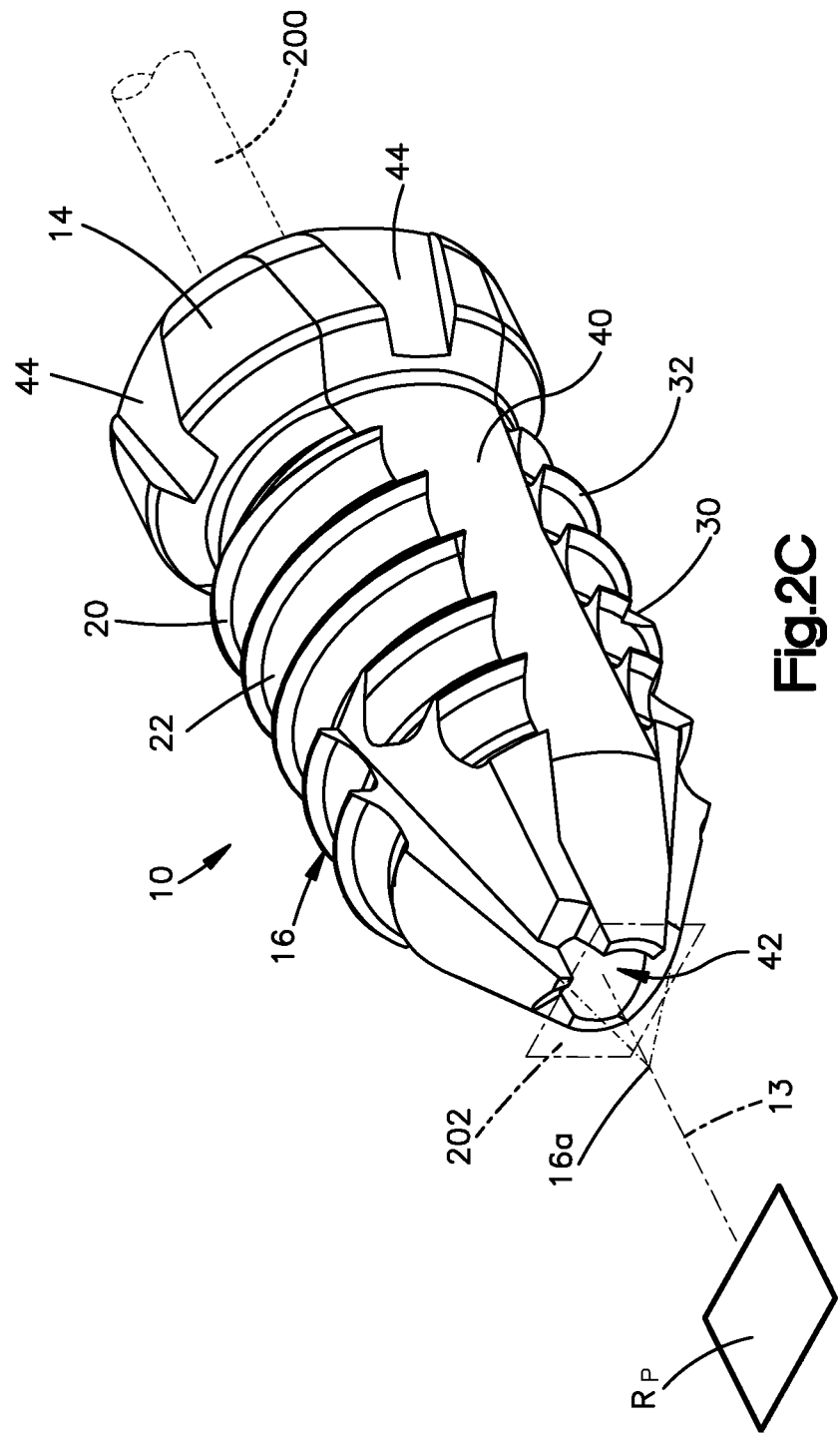
FIG. 2C illustrates a side perspective view of the facet interference screw shown in FIG. 2A, with a temporary spacer.
Figure 3D:
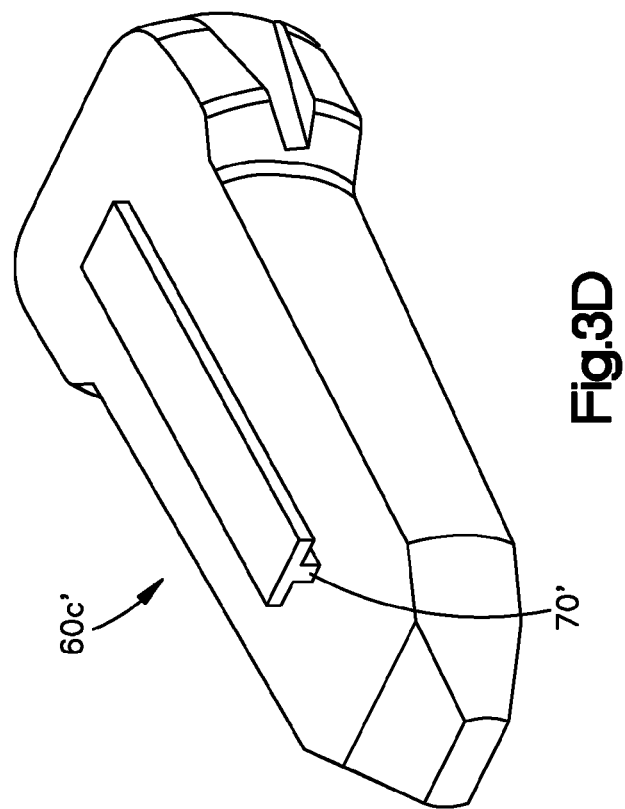
FIG. 3D illustrates a top perspective view of yet another alternate damping component that may be used in connection with the facet interference screw shown in FIG. 3A, the damping component including a T-shaped channel for engaging a groove formed in one or both of a first component and a second component of the facet interference screw of FIG. 3A.
Figure 3C:
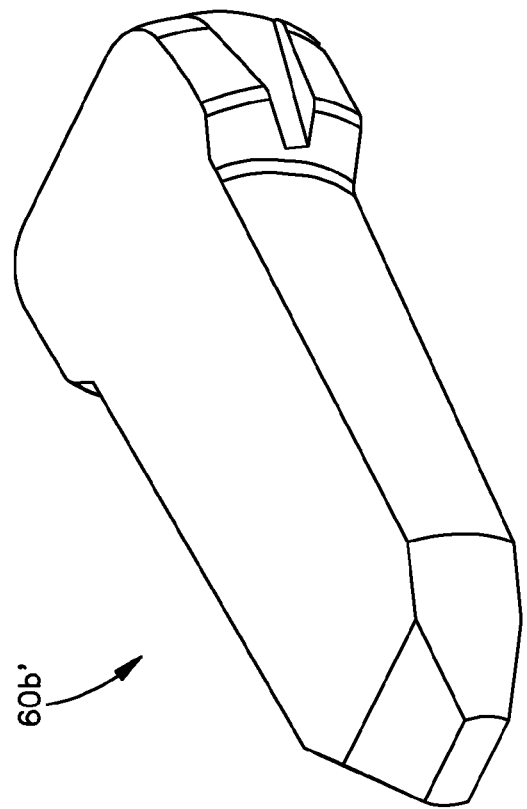
FIG. 3C illustrates a top perspective view of an alternate damping component that may be used in connection with the facet interference screw shown in FIG. 3A, the damping component being generally solid and continuous.
Figure 4A:
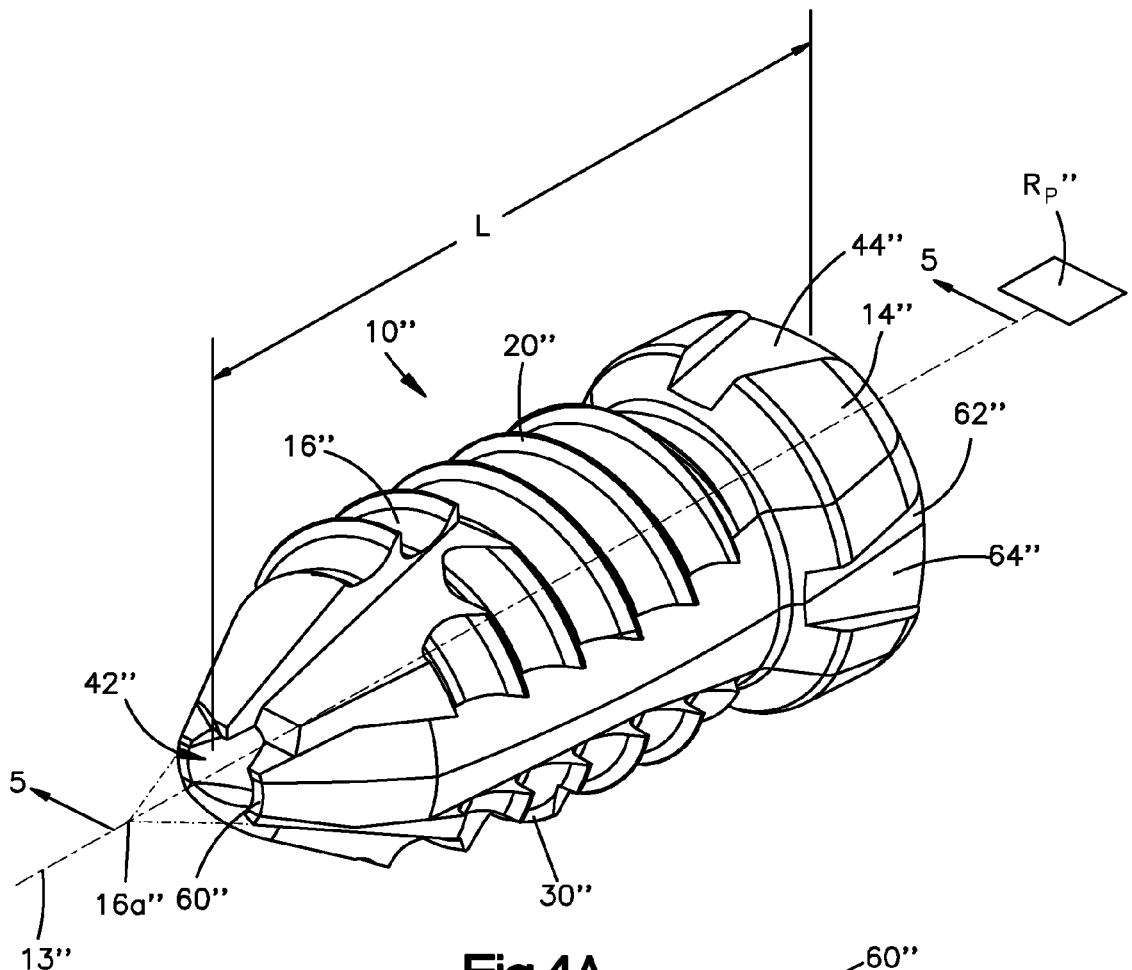
FIG. 4A illustrates a side perspective view of a facet interference screw according to a third preferred embodiment of the present invention.
Figure 4B:
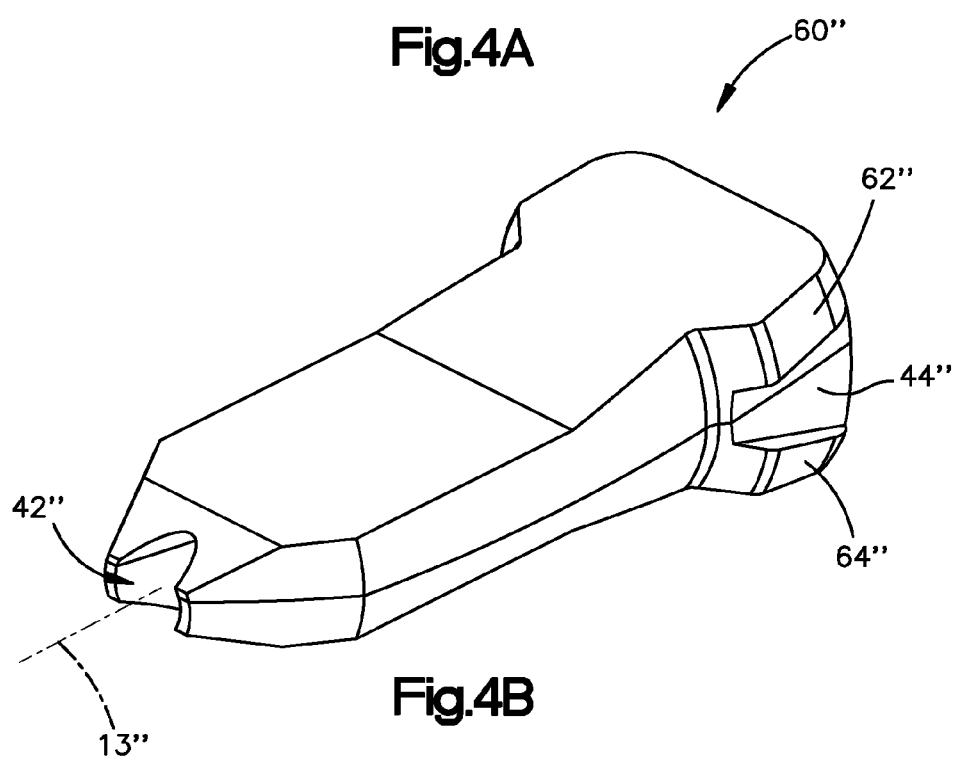
FIG. 4B illustrates a side perspective view of an exemplary two-piece articulating component that may be used in connection with the facet interference screw shown in FIG. 4A.
Figure 5A:
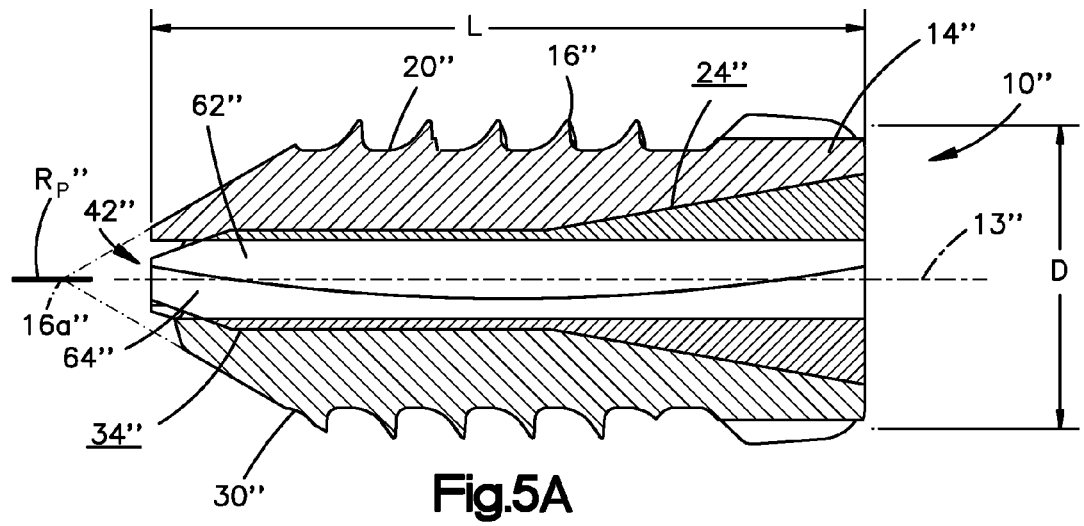
FIG. 5A illustrates a cross-sectional view of the facet interference screw shown in FIG. 4A taken along line 5-5 of FIG. 4A, the facet interference screw shown in a neutral position.
Figure 5B:
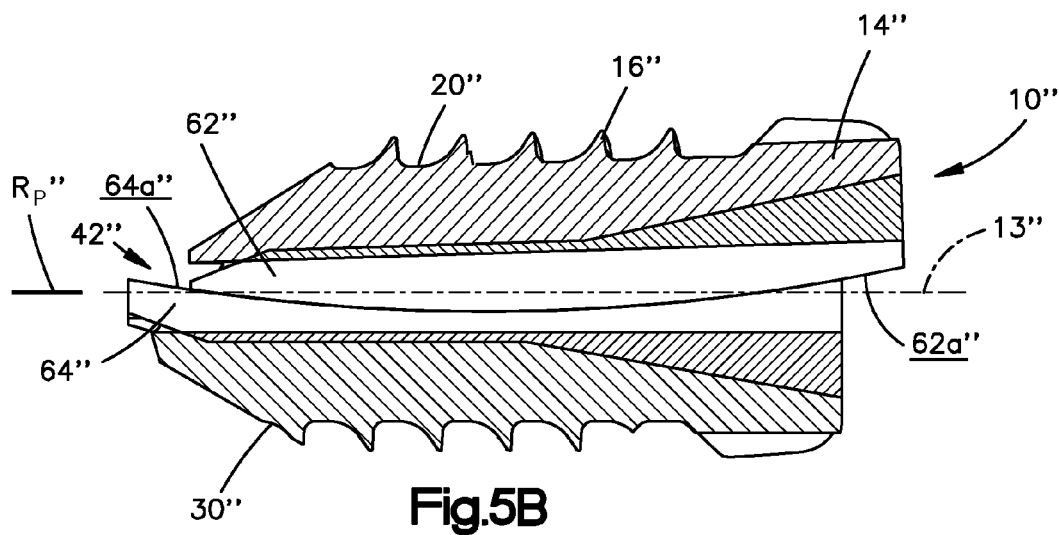
FIG. 5B illustrates a cross-sectional view of the facet interference screw shown in FIG. 4A taken along line 5-5 of FIG. 4A, the facet interference screw shown undergoing flexion.
Figure 5C:
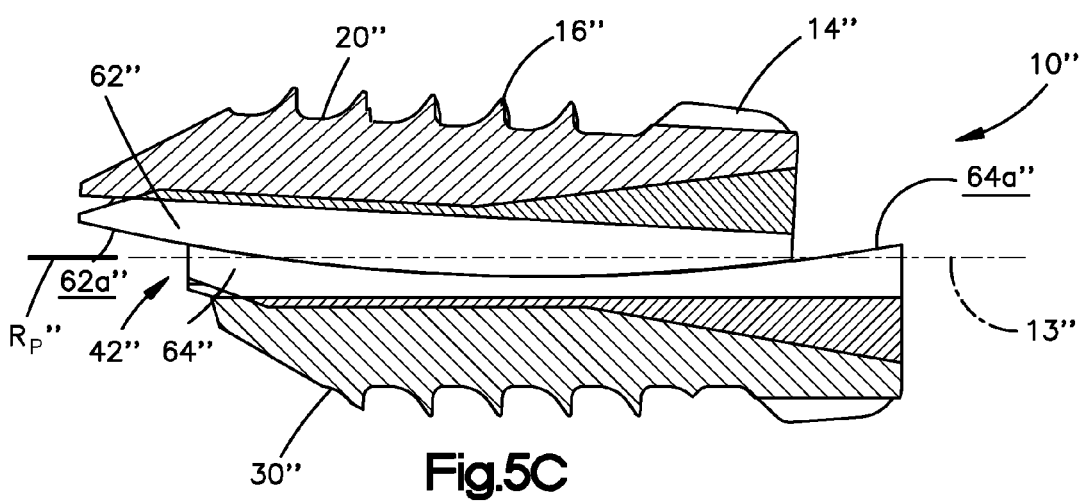
FIG. 5C illustrates a cross-sectional view of the facet interference screw shown in FIG. 4A taken along line 5-5 of FIG. 4A, the facet interference screw shown undergoing extension.

Referring to FIG. 2C, the facet interference screw 10 of the first preferred embodiment may also include a temporary spacer 40 located between the inner surfaces 24, 34 of the first and second components 20, 30, at least in an insertion configuration. Preferably, the temporary spacer 40 includes a cannulated opening 42 for receipt of a guide wire 200 (FIG. 8), as will be described in greater detail below. In use, the temporary spacer 40 is inserted between the inner surfaces 24, 34 of the first and second components 20, 30 in the insertion configuration. The facet interference screw 10 with the temporary spacer 40 mounted therein is inserted between the inferior facet $F_i$ formed on the superior vertebra V and the superior facet $F_S$ formed on the inferior vertebra V via rotation of the facet interference screw 10. Once positioned in the mounted position, the spacer 40 is preferably removed and the inner surfaces 24, 34 move into facing engagement or contact to facilitate motion therebetween. The guide wire 200 may include a larger diameter portion 202 at a distal end that engages and removes the temporary spacer 40 upon removal of the guide wire 200 from the facet joint $FJ_1$, $FJ_2$. In this manner, the spacer 40 facilitates insertion of the facet interference screw 10 of the first preferred embodiment between the inferior facet $F_i$ and the superior facet $F_S$ with the assistance of the guide wire 200. In use, the spacer 40 prevents surface contact between the inner surfaces 24, 34 of the first and second components 20, 30. In the mounted position, removal of the spacer 40 preferably enables the curved inner surfaces 24, 34 to articulate along the curved or arcuate path. In addition, the facet interference screw 10 of the first preferred embodiment is positioned in the mounted position such that the articulation plane $R_P$ of the facet interference screw 10 is generally parallel to the first or second facet joint plane $FJ_{P1}$, $FJ_{P2}$, respectively to facilitate restoration of a near-normal articulation or movement of the respective facet joint $FJ_1$, $FJ_2$.

Referring to FIGS. 3A-3D, a second preferred embodiment of the facet interference screw 10' is similar to the first preferred embodiment of the facet interference screw 10 except that the second preferred embodiment of the facet interference screw 10' includes a damping component 60a', 60b', 60c' located between the inner surfaces (not shown in the second preferred embodiment) of the first and second components 20', 30' to facilitate damping and/or movement of the first and second components 20', 30' with respect to one another. The facet interference screw 10' of the second preferred embodiment is shown with like reference numerals to indicate like elements and a prime symbol (') to distinguish the elements of the facet interference screw 10' of the second preferred embodiment. The preferred damping component 60a', 60b', 60c' preferably facilitates compression of the first and second components 20', 30' with respect to one another. In addition, the preferred damping component 60a', 60b', 60c' enables lateral and longitudinal movement between the first and second components 20', 30'. The damping component 60a', 60b', 60c' is preferably constructed of a relatively elastic material that permits movement in six degrees of freedom between the first and second components 20', 30'. For example, the damping component 60a', 60b', 60c' may be constructed of a polymeric material that is strong enough to withstand the typical loads encountered by the facet interference screw 10' when mounted in the facet joint FJ and is able to withstand the environment encountered during permanent implantation in the facet joint FJ.

The damping component 60a', 60b', 60c' of the second preferred embodiment may be pre-assembled and/or connected to the first and/or second components 20', 30' by any mechanism now or hereafter known in the art including but not limited to an adhesive, a mechanical connection, etc. Alternatively, the damping component 60a', 60b', 60c' may be inserted between the inner surfaces 24', 34' after the first and second components 20', 30' are inserted into the facet joint FJ in a mounted position, either with or without the temporary spacer (not shown in FIGS. 3A-3D). That is, for example, the facet interference screw 10' of the second preferred embodiment may be inserted into the facet joint FJ and the first and second components 20', 30' may then be separated to receive the damping component 60a', 60b', 60c' therebetween.

In the second preferred embodiment, the damping component 60a', 60b', 60c' may have several configurations including a first preferred damping component 60a' that includes the cannulated opening 42' therein, a second preferred damping component 60b' that is generally solid and continuous and a third preferred damping component 60c' that includes a guiding and locking mechanism 70'. The first preferred damping component 60a' includes the cannulated opening 42' to accommodate the guide wire 200 therein during implantation of the facet interference screw 10'. The first preferred damping component 60a' is preferably, permanently bonded to the first and second components 20', 30' prior to implantation in the facet joint FJ. The second preferred damping component 60b' includes a generally solid, integral configuration without the cannulated opening 42'. The second preferred damping component 60b' may be permanently bonded or joined to the first and second components 20', 30' or may be inserted between the first and second components 20', 30' following initial implantation and removal of the spacer 40' (not shown in FIGS. 3A-3D). A third preferred damping component 60c' preferably includes a guiding and locking mechanism 70' to facilitate insertion of the damping component 60c' between the first and second components 20', 30'. The guiding and locking mechanism 70' may be comprised of any mechanism now or hereafter known including, but not limited to, a tongue and groove system. For example, the inner surface 24', 34' of at least one of the first and second components 20', 30' may include a groove (not shown) for mating with the T-shaped locking mechanism 70' extending from the damping component 60'. In addition, the surfaces of the first and second preferred damping components 60a', 60b' that mate with the first and second components 20', 30' are not limited to being generally flat and continuous, as is shown in the Figs., but may include engagement features or may be generally rough in order to facilitate engagement and mating with the inner surfaces of the first and second components 20', 30'. For example, the first, second and/or third damping components 60a', 60b', 60c' may be injection molded to the first and second components 20', 30', which have roughened, grooved, spiked or otherwise uneven inner surfaces to assist in retaining the damping components 60a', 60b', 60c' to the first and second components 20', 30'.

Referring to FIGS. 4A-6B, a third preferred embodiment of the facet interference screw 10" includes a two-piece damping component 60", although three or more pieces are also contemplated. The facet interference screw 10" of the third preferred embodiment is shown with like reference numerals to indicate like elements and a double prime symbol (") to distinguish the elements of the facet interference screw 10" of the third preferred embodiment. The two-piece damping component 60" preferably includes an upper damping component 62" mounted to the inner surface 24" of the first component 20" and a lower damping component 64" mounted to the inner surface 34" of the second component 30". The upper and lower damping components 62", 64" preferably each include curved contacting surfaces 62a", 64a" so that the upper damping component 62" is movable with respect to the lower damping component 64" and the first component 20" is movable with respect to the second component 30". More preferably, the curved contacting surfaces 62a", 64a" formed on the upper and lower damping components 62", 64" preferably have corresponding spherical surfaces in both the longitudinal direction (e.g., parallel to the longitudinal axis 13") and in the lateral direction (e.g., perpendicular to the longitudinal axis 13"). In this manner, the spherical curved contacting surfaces 62a", 64a" facilitate flexion/extension articulation and lateral articulation, as illustrated in FIGS. 5A-6B. The inner surfaces 24", 34" may also facilitate the cannulated opening 42" for receipt of the guide wire 200 to guide implantation of the facet interference screw 10" of the third preferred embodiment. However, the facet interference screw 10" of the third preferred embodiment is not limited to inclusion of the cannulated opening 42" and may be constructed without the cannulated opening 42" such that the upper and lower damping components 62a", 64a" are in contact along substantially their entire spherical curved contacting surfaces 62a", 64a" in the assembled configuration.

The upper and lower damping components 62", 64" are preferably constructed of a polymeric material that provides some elasticity, but also is rigid enough to resist significant wear at the curved contacting surfaces 62a", 64a" during use in the mounted position. For example, the upper and lower damping components 62", 64" may be constructed of a polyetheretherketone (PEEK) material, but is not so limited and may be constructed of nearly any material that provides damping and wear capability and is able to withstand the normal operating conditions and environment of the mounted position. In addition, the first and second components 20", 30" are preferably constructed of a metallic material, such as titanium or steel, but is not so limited and may be constructed of nearly any biocompatible material that is able to take on the general shape of the first and second components 20", 30" and withstand the normal operating conditions of the facet interference screw 10".

Referring to FIGS. 7A and 7B, the facet interference screws 10, 10', 10" of the first, second and third preferred embodiments may also include an anti-rotational mechanism or feature 100a, 100b to inhibit the facet interference screws 10, 10', 10" from backing out of the mounted position. For example, a first anti-rotational mechanism 100a may be in the form of a spacer 100a that is inserted between the first and second components 20, 30 so that the profile of the facet interference screws 10, 10', 10" is no longer circular in the mounted position and thus less likely to back-out or otherwise rotate in the mounted position. The spacer 100a is preferably constructed of a damping-type material to permit limited movement between the first and second components 20, 30. More preferably, as shown in FIG. 7B, a second preferred anti-rotational spacer 100b may have a width wider than the diameter of the facet interference screw 10, 10', 10" in at least one portion of its length, thereby further inhibiting back out. The anti-rotational mechanism 100a, 100b may be separate and distinct from the preferred damping components 60a', 60b', 60c', 60" or may be integrally formed therewith. Alternatively, the facet interference screw 10, 10', 10" may incorporate an anti-rotation mechanism having a U-shape, as is disclosed in U.S. Published Patent Application No. 2006/0064099, titled Articular Facet Interference Screw and filed Nov. 13, 2002, which is incorporated herein by reference in its entirety.

Referring to FIGS. 2A, 3A, 4A, 5A, 6A and 7A, the facet interference screws 10, 10', 10" of the preferred embodiments preferably have a screw diameter D and a screw length L. The screw length L is preferably between five (5) and twenty-five (25) millimeters and the screw diameter D is preferably between four (4) and eleven (11) millimeters. The facet interference screws 10, 10', 10" are not limited to these dimensions, but preferably fall within these ranges to permit the minimally invasive insertion of the facet interference screws 10, 10', 10" into the facet joints FJ, to limit the extension of the tip 16a through the facet joints FJ, to permit the facet interference screws 10, 10', 10" to travel through a cannula (not shown) during a minimally invasive procedure and for other related considerations. In addition, the facet interference screws 10, 10', 10" of the preferred embodiments preferably include the head portion 14, 14', 14" to facilitate engagement by an insertion and/or removal tool and to inhibit the distance that the facet interference screws 10, 10', 10" are inserted into the facet joints FJ.

Referring to FIGS. 6A-7B, the facet interference screws 10, 10', 10" of the preferred embodiments may include an articulation indicator 50, 50" on the head 14, 14" that aligns with the articulation plane $R_P$ of the facet interference screw 10, 10', 10". The articulation indicator 50, 50" provides a visual indicator to the surgeon to verify that the articulation plane $R_P$ of the facet interference screw 10, 10', 10" is aligned with the facet joint planes $FJ_{P1}$, $FJ_{P2}$ in the mounted position. Misalignment or misorientation of the articulation plane $R_P$ typically limits the facet interference screw 10, 10', 10" from operating in its intended manner and may result in a fusion of the facet joints FJ. Alternatively, the surgeon may elect to insert the facet interference screw 10, 10', 10" such that the articulation plane $R_P$ is misaligned with the facet joint planes $FJ_{P1}$, $FJ_{P2}$ such that fusion is intentionally promoted in the facet joints FJ. Further, the articulation indicator 50, 50" may be curved or otherwise provide an indication that the inner surfaces 24, 34 are curved to create a curved articulation path such that the surgeon is able to arrange the articulation plane $R_P$ with the naturally curved articulation of the facet joints FJ.

Figure 8:
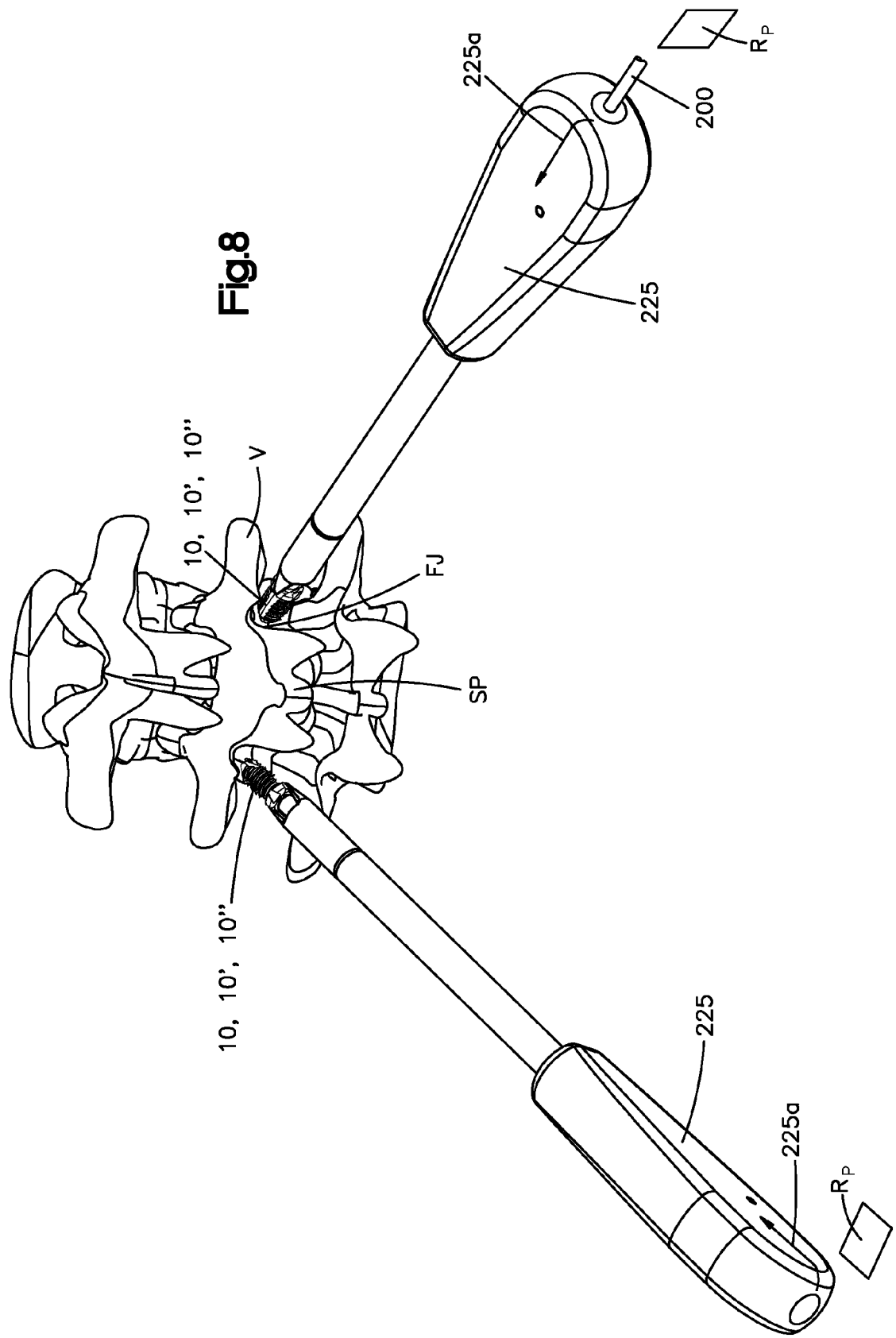
FIG. 8 illustrates a rear perspective view of two facet interference screws in accordance with at least one of the first, second and third preferred embodiments being simultaneously inserted into facet joints of a patient's spine in accordance with a preferred method of the present invention.

In use, the facet interference screws 10, 10', 10" of the preferred embodiments are self-tapping and/or self-drilling. The first and second components 20, 30 are preferably pre-assembled either alone or in connection with a preferred temporary spacer 40 and/or damping component 60a', 60b', 60c', 60" by, for example, a rigid connection in the screw head 14 so that, in use, the facet interference screw 10, 10', 10" can be inserted by, rotating the facet interference screw 10, 10', 10" into the facet joints FJ via a screw driver 225, as shown in FIG. 8. Preferably, the articulation plane $R_P$ of the facet interference screws 10, 10', 10" are aligned with the facet joint planes $FJ_{P1}$, $FJ_{P2}$ in the mounted position to permit articulation of the facet joints FJ with the facet interference screws 10, 10', 10" mounted therein. Alternatively, the articulation plane $R_P$ may be intentionally misaligned with the facet joint planes $FJ_{P1}$, $FJ_{P2}$ to promote fusion or limit movement in the facet joints FJ.

Figure 9D:
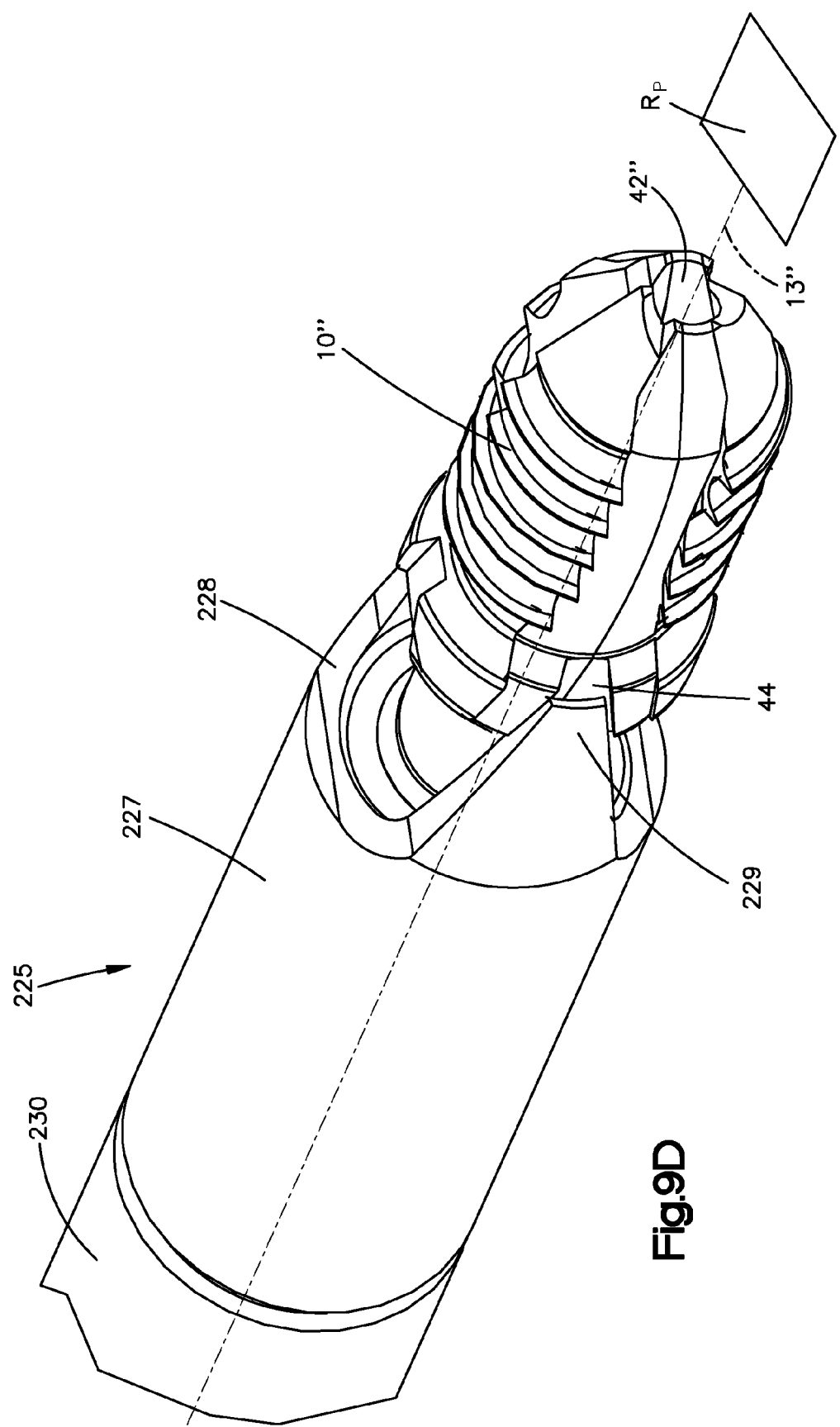
FIG. 9D illustrates an enlarged top perspective view of the facet interference screw of FIG. 4A mounted to the screw driver with the sleeve in a further retracted position.

Referring to FIGS. 9A-9D, a preferred screw driver 225 for inserting, implanting and/or driving the facet interference screws 10, 10', 10" into the facet joints FJ includes a mechanism to secure the first and second components 20, 30 and any additional component parts together and to maintain adequate torque during insertion. The preferred screw driver 225 includes a shaft 227 and a sleeve 230. The shaft 227 preferably includes a tip 228 for simultaneously engaging the first and second components 20, 30 of the facet interference screw 10, 10', 10". The tip 228 preferably includes a plurality of projections 229 for engaging a plurality of recesses 44 formed in the head portion 14 of the facet interference screw 10, 10', 10". The sleeve 230 is preferably movably disposed over the shaft 227 from an extended position (as shown in phantom lines in FIGS. 9A and 9B) wherein the sleeve 230 encapsulates the facet interference screw 10, 10', 10" coupled to the distal end of the screwdriver 225, to a retracted position (as shown in FIG. 9C) wherein the facet interference screw 10, 10', 10" coupled to the distal end of the screwdriver 225 is exposed. The sleeve 230 is preferably biased via, for example, a spring 235 to the extended position.

The screwdriver 225 also preferably includes an indicator 225a at a proximal end of the handle of the screwdriver 225 to provide an indication of the articulation plane $R_P$ of the facet interference screw 10, 10', 10". The facet interference screw 10, 10', 10" is preferably mountable onto the screwdriver 225 in a single orientation such that the indicator 225a aligns with the articulation plane $R_P$ of the screw facet interference screw 10, 10', 10". Accordingly, the surgeon is able to verify the orientation of the articulation plane $R_P$ in the mounted position to align with the facet joint planes $FJ_{P1}$, $FJ_{P2}$ to promote articulation or in misalignment to promote fusion, as is apparent to one having ordinary skill in the art based upon a review of the present disclosure.

In use, the user preferably moves the sleeve 230 to the retracted position so that the facet interference screw 10, 10', 10" may be coupled to the distal end of the screwdriver 225. The sleeve 230 moves via the spring bias into the extended position so that the facet interference screw 10, 10', 10" is encapsulated by the sleeve 230. In the extended position, the sleeve 230 assists in maintaining the first and second components 20, 30 of the facet interference screw 10, 10', 10" together so that the multiple components of the facet interference screw 10, 10', 10" can be rotated as a single unit into the facet joints FJ. During insertion, contact between the distal end of the sleeve 230 and the patient's bone moves the sleeve 230 from the extended position to the retracted position to expose the facet interference screw 10, 10', 10". The facet interference screw 10, 10', 10" is driven into the facet joint FJ until the head 14 contacts the bone of the facet joint FJ and the surgeon preferably aligns the indicator 225a with the facet joint planes $FJ_{P1}$, $FJ_{P2}$.

Primary fixation of the facet interference screw 10, 10', 10" into the facet joints FJ may be achieved by the external threads on the shaft portion 16 of the facet interference screw 10, 10', 10" engaging the superior and inferior facets $F_S$, F. Secondary fixation may be achieved by osteo-integration. For example, the facet interference screws 10, 10', 10", and in particular the external threads formed on the shaft portion 16 of the facet interference screws 10, 10', 10", may be roughened and/or coated for osteo-conduction. The facet interference screws 10, 10', 10" may be coated with any bioactive coating now or hereafter known including, but not limited to, Ti-Plasma spray, anodic surface enhancement such as, for example, APC, HA or any Ca—P enhancement, etc.

The preferred facet interference screws 10, 10', 10" and the anti-rotational mechanisms 100, 100' may be manufactured from any biocompatible material known in the art including but not limited to stainless steel, titanium, titanium alloy, a polymer such as, for example, PPEK, PEKK, PEK, PEKK-EK with or without an optional carbon fiber reinforcement, etc., a ultra-high-molecular-weight polyethylene (UHMWPE), cobalt-chromium-molybdenum (CCM), etc.

The damping components 60a', 60b', 60c', 60" may be manufactured from any biocompatible material known in the art including but not limited an elastomeric-thermoplastic polymer (PCU or polymerized Silicone), a member of PUR or Silicone family, a copolymer, etc. Preferably the damping components 60a', 60b', 60c', 60" has a profile (e.g., size and shape) that matches or substantially matches the profile (e.g., size and shape) of the first and second components 20, 30. The damping components 60a', 60b', 60c', 60" may be coated, either partially or completely, to reduce the amount of wear. For example, the damping components 60a', 60b', 60c', 60" may be coated with any metal carbide or nitride, member of the DLC family, $Al_2O_3$, $ZrO_2$, TiC, TiN, (A)DLC, CrN, CrC, etc.

Surgical Technique

The facet interference screws 10, 10', 10" of the first, second and third preferred embodiments may be inserted by any surgical technique known in the art. The facet interference screws 10, 10', 10" may be inserted percutaneously, similar to the insertion of the facet interference screw disclosed in U.S. patent application Ser. No. 11/126,976, entitled Articular Facet Interference Screw, which was filed on May 10, 2005 and is assigned to the Synthes (U.S.A.), the entire contents of which is incorporated herein by reference.

Referring to FIG. 8, in use, the facet interference screws 10, 10', 10" of the first, second and third preferred embodiments are inserted into the facet joint FJ via a minimally invasive procedure. It is envisioned that the facet interference screws 10, 10', 10" may also be inserted through an open surgery. In one exemplary method of inserting the facet interference screws 10, 10', 10", the guide wire 200 is introduced percutaneously into each of the facet joints FJ between the adjacent superior and inferior vertebra V. The introduction of the guide wires 200 may be guided into the facet joints FJ by any means including, but not limited to C-arm imaging, CT-scan, a mini-open approach to the facet joints FJ, etc. After verifying the symmetrical position of the guide wires 200, an optional tissue protection sleeve, cannula, retractor and/or trocar (not shown) may be guided to the facet joint FJ to open a path to the facet joint FJ. The facet interference screws 10, 10', 10" are introduced into the facet joints FJ, preferably via the guide wires 200 and through the protection sleeve, cannula, retractor or trocar. Thereafter, the orientation of the facet interference screw 10, 10', 10" is preferably verified, and the guide wires 200, instrumentation and temporary spacer 40 (if required) are removed. If necessary, the damping component 60a', 60b', 60c', 60" and the anti-rotational mechanism 100a, 100b, if desired, may be inserted between the inner surfaces 24, 34 of the first and second components 20, 30. The orientation of the articulation plane $R_P$ is verified by one or both of the indicators 50, 225a, specifically with respect to the facet joint planes $FJ_{P1}$, $FJ_{P2}$.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

The invention claimed is:

1. A facet interference screw for insertion into a facet joint between an inferior facet of a superior vertebra and a superior facet of an inferior vertebra, the facet interference screw being elongate along a central longitudinal axis, the facet interference screw comprising:
   a first component including a first outer semicircular surface and a first inner surface, the first outer semicircular surface intersecting with the first inner surface to define a first edge and a second edge that is spaced from the first edge in a direction direction perpendicular to the central longitudinal axis; and
   a second component including a second outer semicircular surface and a second inner surface, the second outer semicircular surface intersecting with the second inner surface to define a third edge and a fourth edge that is spaced from the third edge in a second direction perpendicular to the central longitudinal axis, the first and second components, when assembled with each other, define a head, a tip spaced from the head along the central longitudinal axis, and an externally threaded shaft portion extending between the head and the tip, the externally threaded shaft portion including a first thread extending uninterrupted from the first edge to the second edge along the first outer semicircular surface, the externally threaded shaft portion further including a second thread extending uninterrupted from the third edge to the fourth edge along the second outer semicircular surface, wherein when the first and second components are assembled with each other the first and second threads align to facilitate rotational implantation into the facet joint;
   an upper inner component having a respective outer surface configured to at least partially abut the first inner surface of the first component and a first contact surface that extends from a first location near the head to a second location near the tip; and
   a lower inner component having a respective outer surface configured to at least partially abut the second inner surface of the second component and a second contact surface that extends from a third location near the head to a fourth location near the tip, the second contact surface configured to engage with the first contact surface such that the upper inner component is articulable with respect to the lower inner component.

2. The facet interference screw of claim 1, wherein a respective first one of the first or second contacting surfaces is convex and a respective second one of the first or second contacting surfaces is concave.

3. The facet interference screw of claim 2, wherein a respective radius of curvature of the convex surface is substantially equal to a respective radius of curvature of the concave surface.

4. The facet interference screw of claim 1, wherein the first and second inner surfaces are generally parallel.

5. The facet interference screw of claim 1, wherein the first and second inner surfaces are curved.

6. The facet interference screw of claim 1, wherein at least one of the first and second inner surfaces includes a guiding mechanism.

7. The facet interference screw of claim 1, wherein at least a portion of the first contacting surface is substantially spherical and at least a portion of the second contacting surface is substantially spherical.

8. The facet interference screw of claim 1, wherein the head includes an indicator that is aligned with an articulation plane defined by the facet interference screw.

9. The facet interference screw of claim 1, wherein the respective outer surface of the upper inner component is bonded to the first inner surface and the respective outer surface of the lower inner component is bonded to the second inner surface.

10. The facet interference screw of claim 1, wherein the upper and lower inner components define a cannulation that extends through the facet interference screw along the central longitudinal axis.

11. The facet interference screw of claim 1, wherein the first and third locations are disposed substantially at the head and the second and fourth locations are disposed substantially at the tip.

12. The facet interference screw of claim 1, wherein the first and third locations are substantially coincident with one another and the second and fourth locations are substantially coincident with one another.

13. The facet interference screw of claim 1, wherein the externally threaded shaft portion is substantially circular in shape.

14. The facet interference screw of claim 1, wherein the tip defines a first maximum outer dimension, the externally threaded shaft portion defines a second maximum outer dimension that is greater than the first maximum outer dimension, and the head defines a third maximum outer dimension that is greater than the second maximum outer dimension, each of the first, second, and third maximum outer dimensions being measured in a direction perpendicular to the central longitudinal axis.

15. The facet interference screw of claim 1, wherein the first direction perpendicular to the central longitudinal axis and the second direction perpendicular to the central longitudinal axis are the same direction.

16. A method comprising the steps of:
providing a facet interference screw including a first component having a first externally threaded surface and a first inner surface and a second component having a second externally threaded surface and a second inner surface, the first and second components defining a tip and a head of the facet interference screw;
inserting a spacer between the first and second inner surfaces of the first and second components of the facet interference screw, the spacer defining a cannula that extends through the spacer;
inserting a guide wire at least partially into a facet joint between a first vertebra and a second vertebra that is adjacent the first vertebra;
disposing the cannula over the guide wire and guiding the facet interference screw along the guide wire such that the tip of the facet interference screw is positioned adjacent the facet joint;
driving the facet interference screw into the facet joint until the head contacts at least one of the first or second vertebrae; and
removing the guide wire from the facet joint such that the guide wire engages the cannula and causes the spacer to be withdrawn from between the first and second inner surfaces of the first and second components.

17. The method of claim 16, further comprising the steps of:
providing a second facet interference screw including a first component having a first externally threaded surface and a first inner surface and a second component having a second externally threaded surface and a second inner surface, the first and second components defining a tip and a head of the second facet interference screw;
inserting a second spacer between the first and second inner surfaces of the first and second components of the second facet interference screw, the spacer defining a cannula that extends through the spacer;
inserting a guide wire at least partially into a second facet joint between the first vertebra second vertebrae;
disposing the cannula of the second spacer over the second guide wire and guiding the second facet interference screw along the second guide wire such that the tip of the second facet interference screw is positioned adjacent the second facet joint;
driving the second facet interference screw into the second facet joint until the head contacts at least one of the first or second vertebrae; and
removing the second guide wire from the second facet joint such that the guide wire engages the cannula of the second spacer and causes the second spacer to be withdrawn from between the first and second inner surfaces of the first and second components of the second facet interference screw.

18. The method of claim 17, further comprising the step of:
prior to removing the guide wire and the second guide wire, inserting a first damping component between the first and second inner surfaces of the first and second components of the facet interference screw and inserting a second damping component between the first and second inner surfaces of the first and second components of the second facet interference screw.

19. The method of claim 18, wherein the each of the first and second damping components comprises an upper inner component having a first contact surface and a lower inner component having a second contact surface configured to abut the first contact surface such that the upper and lower inner components are articulable with respect to each other along the first and second contact surfaces.

20. The method of claim 17, wherein the facet interference screw and the second facet interference screw are driven into the facet joint and the second facet joint, respectively, substantially simultaneously.

21. The method of claim 17, wherein the method further comprises the step of:
prior to guiding the facet interference screw along the guide wire and guiding the second facet interference screw along the second guide wire, verifying that a position of the guide wire in the facet joint is substantially symmetrical with respect to a respective position of the second guide wire in the second facet joint.

22. The method of claim 16, further comprising the step of:
prior to removing the guide wire, inserting a damping component between the first and second inner surfaces of the first and second components.

23. The method of claim 16, wherein the head includes an indicator that represents an articulation plane of the facet interference screw, the method further comprising the step of:
aligning the indicator with a facet joint plane of the facet joint.

* * * * *